(12) United States Patent
Wendler et al.

(10) Patent No.: US 9,743,898 B2
(45) Date of Patent: Aug. 29, 2017

(54) IMAGE FORMATION APPARATUS AND METHOD FOR NUCLEAR IMAGING

(71) Applicants: Thomas Wendler, Munich (DE); Nassir Navab, Munich (DE); Jörg Traub, Munich (DE)

(72) Inventors: Thomas Wendler, Munich (DE); Nassir Navab, Munich (DE); Jörg Traub, Munich (DE)

(73) Assignee: Surgiceye GmbH, Munich (DE)

( * ) Notice: Subject to any disclaimer, the term of this patent is extended or adjusted under 35 U.S.C. 154(b) by 252 days.

(21) Appl. No.: 14/738,560

(22) Filed: Jun. 12, 2015

(65) Prior Publication Data

US 2015/0305701 A1    Oct. 29, 2015

Related U.S. Application Data

(63) Continuation of application No. 12/601,800, filed as application No. PCT/EP2008/056433 on May 26, 2008, now abandoned.

(30) Foreign Application Priority Data

May 24, 2007  (EP) .................................. 07010368
May 24, 2007  (EP) .................................. 07010369

(51) Int. Cl.
*G06K 9/00*       (2006.01)
*A61B 6/00*       (2006.01)
(Continued)

(52) U.S. Cl.
CPC ............ *A61B 6/5205* (2013.01); *A61B 6/037* (2013.01); *A61B 6/4258* (2013.01); *G01T 1/161* (2013.01)

(58) Field of Classification Search
USPC .................................................. 382/128–134
See application file for complete search history.

(56) References Cited

U.S. PATENT DOCUMENTS 5,666,444 A * 9/1997 Kawamura .............. H04N 1/52
                                                    382/270
6,167,296 A   12/2000 Shahidi
                    (Continued)

FOREIGN PATENT DOCUMENTS

EP    1237012 A2    9/2002
JP    0900-5441     1/1997
            (Continued)

OTHER PUBLICATIONS

Kang-Ping et al. "A General Technique for Interstudy Registration of Multifunction Registration of Multifunction and Multimodality Images", IEEE Transactions on Nuclear Science, IEEE Service Center, New York, NY, US, Bd 41, Nr. 6, Dec. 1, 1994.
(Continued)

*Primary Examiner* — Alex Liew
(74) *Attorney, Agent, or Firm* — Patterson + Sheridan LLP

(57) ABSTRACT

An image generating apparatus for image generation is provided. The image generating apparatus includes a movable detector for detecting nuclear radiation during a detection period and an evaluation system. The evaluation system includes an interface system for transmitting detector data to the evaluation system. The detector data include information about the detected radiation for image generation. The evaluation system further includes a data memory portion for storing the detector data. The evaluation system further includes a program memory portion with a program for repeatedly determining at least one quality value with respect to image generation during the detection period.

20 Claims, 14 Drawing Sheets

(51) Int. Cl.
*G01T 1/161* (2006.01)
*A61B 6/03* (2006.01)

(56) References Cited

U.S. PATENT DOCUMENTS

| | | | |
|---|---|---|---|
| 6,510,336 B1 | 1/2003 | Daghighian et al. | |
| 6,674,916 B1* | 1/2004 | Deman | G06T 3/0068 |
| | | | 382/128 |
| 6,804,325 B1* | 10/2004 | Smith | G01T 1/2985 |
| | | | 250/363.02 |
| 7,068,854 B1* | 6/2006 | Aufrichtig | G06T 5/20 |
| | | | 250/208.1 |
| 2001/0038706 A1* | 11/2001 | Eck | G06T 5/20 |
| | | | 382/132 |
| 2002/0156366 A1 | 10/2002 | Stainsby et al. | |
| 2004/0054248 A1 | 3/2004 | Kimchy et al. | |
| 2004/0204646 A1 | 10/2004 | Nagler et al. | |
| 2006/0093213 A1 | 5/2006 | Steinberg et al. | |
| 2007/0236514 A1 | 10/2007 | Agusanto et al. | |
| 2008/0219534 A1* | 9/2008 | Faul | A61B 6/032 |
| | | | 382/131 |
| 2009/0046917 A1* | 2/2009 | Konishi | G06T 3/4007 |
| | | | 382/132 |
| 2009/0123042 A1* | 5/2009 | Gagnon | G06T 3/4061 |
| | | | 382/128 |
| 2010/0266171 A1* | 10/2010 | Wendler | G01T 1/161 |
| | | | 382/128 |
| 2014/0369560 A1* | 12/2014 | Wendler | A61B 6/4258 |
| | | | 382/103 |

FOREIGN PATENT DOCUMENTS

| | | |
|---|---|---|
| JP | 2004-512502 A | 4/2004 |
| WO | 2007131561 A2 | 11/2007 |

OTHER PUBLICATIONS

Fei et al. "Automatic Registraction of CT Volumes and Dual-Energy Digital Radiography for Detection of Cardiac and Lung Diseases", Aug. 30, 2006.

Thomas Wendler et al. "Navigated Three Dimensional Beta Probe for Optimal Cancer Resection", Jan. 1, 2006. Medical image computing and Computer-Assisted Intervention—MICCAI 2006 Lecture Notes in Computer Science.

EP Search Report dated Jul. 22, 2014 for Application No. EP 14 16 4239.

Translation of Japanese Office Action, Application No. 2010-508870, dated May 14, 2013.

International Search Report by ISA/EPO, in PCT/EP2008/056433, dated Feb. 24, 2009.

* cited by examiner

IMAGE FORMATION APPARATUS AND METHOD FOR NUCLEAR IMAGING

The present invention relates to image generating apparatuses and methods for image generation with image generating apparatuses. Specific embodiments of the invention relate to image generating apparatuses for enhanced image generation by means of quality control, instruction to a user for data collection and/or a continuous data collection with enhanced processing. Typical embodiments of the present invention relate to image generating apparatuses and methods for medical purposes.

BACKGROUND

High quality image generation is of great interest for a vast area of applications. In particular, in the medical field where the health of patient can depend thereon, the best possible image generation is necessary, for example as a basis for surgery on the patient.

Usually, medical images are generated either pre-operatively or intra-operatively. Also a registration of images is known, for example the registration of an anatomical image with a functional image, i.e., an image that visualizes body activity. Such registered images can for example help in tumor surgeries to decide which body tissue is to be cut out. Images that are as up-to-date and of as high quality as possible are desirable because in this way it can be avoided to damage healthy tissue or not to remove deceased tissue.

The generation of high quality images poses high demands on detector data for image generation and on an evaluation system that must process these data. This is particularly true for processing of detector data with movable detectors which may for example be hand-held.

Consequently there is a need for an enhanced collection and evaluation of detector data and an enhanced image generation.

SUMMARY

In light of the above, one embodiment provides a device for intra-operative 3D-nuclear imaging, 3D-visualization and image-guided surgery based on pre-operative data and tracked radiation detectors, wherein the device includes: (a) a radiation detector; (b) a tracking system for synchronously tracking the position and orientation of said radiation detector and for readout; (c) a pre-operative nuclear image; (d) a data processing system which communicates with the radiation detector and with the tracking system and is adapted to read the pre-operative nuclear image for allowing a three dimensional reconstruction of the nuclear image and/or the computation of a corresponding quality value from a list of readout data, positions and orientations of the radiation device and the pre-operative nuclear image; and (e) a display for displaying the reconstructed image. Another embodiment provides an image generating apparatus for image generation, comprising: a movable detector for detecting nuclear radiation during a detection period; and an evaluation system, comprising: an interface system for transmitting, to the evaluation system, detector data with information about the detected nuclear radiation for image generation, a data memory portion for storing the detector data, and a program memory portion with a program for repeatedly determining at least one quality value with respect to image generation from the detector data during the detection period.

According to one embodiment of the invention, an image generating apparatus for image generation is provided. The image generating apparatus includes a movable detector for detecting nuclear radiation during a detection period. The image generating apparatus further includes an evaluation system. The evaluation system includes an interface system for transmitting detector data to the evaluation system. The detector data include information about the detected nuclear radiation for image generation. The evaluation system further includes a data memory portion for storing the detector data. The evaluation system further includes a program memory portion with a program for repeatedly determining at least one quality value with respect to image generation from the detector data during the detection period.

According to a further embodiment of the present invention an image generating apparatus for image generation is provided. The image generating apparatus includes a freely movable detector for detecting radiation during a detection period. The image generating apparatus further includes an evaluation system. The evaluation system includes an interface system for continuously transmitting detector data to the evaluation system during the detection period. The detector data include information about the detected radiation and information about the position and/or orientation of the detector for image generation. The evaluation system further includes a data memory portion for storing the detector data and a program memory portion with a program for determining at least one quality value with respect to the image generation from the detector data.

According to a further embodiment of the invention, an image generating apparatus for image generation is provided. The image generating apparatus includes a freely movable detector for detection of radiation during a detection period. The image generating apparatus further includes an evaluation system. The evaluation system includes an interface system for continuously transmitting detector data for image generation during a detection period. The detector data include information about the detected radiation. The detector data further include information about the position and/or orientation of the detector. The evaluation system further includes a data memory portion for storing detector data. The evaluation system further includes a program memory portion with a program for determining at least one quality value with respect to image generation from the detector data.

According to a further embodiment of the invention, an image generating apparatus for image generation is provided. The image generating apparatus includes a movable detector for detecting radiation. The image generating apparatus further includes an evaluation system. The evaluation system includes an interface system for transmitting detector data for image generation to the evaluation system. The detector data include information about the detected radiation. The detector data further include information about the position and/or orientation of the detector. The evaluation system further includes a data memory portion for storing detector data. The evaluation system further includes a program memory portion with a program for determining an image generation rule for image generation on the basis of the collected detector data, taking into account a detection model. The detection model takes into account a material property of a material influencing the detection and/or a constraint.

According to a further embodiment, an image generating apparatus for image generation is provided. The image generating apparatus includes a movable detector for detection of radiation. The image generating apparatus further includes an evaluation system. The evaluation system includes an interface system for transmitting detector data for image generation to the evaluation system. The evaluation system further comprises a program memory portion with a program for registering detector data with compatible data.

According to a further embodiment, an image generating apparatus for image generation is provided. The image generating apparatus includes a movable detector for detection of nuclear radiation during a detection period. The image generating apparatus further includes an evaluation system. The evaluation system includes an interface system for transmitting detector data for image generation to the evaluation system. The detector data include information about the detected nuclear radiation. The evaluation system further includes a data memory portion for storing detector data. The evaluation system further includes a program memory portion with a program for determining an image generation rule on the basis of the collected detector data. The evaluation system further includes a program memory portion with a program for repeatedly modifying the image generation rule on the basis of at least one quality value during the detection period.

According to a further embodiment, a method for image generation by means of an image generating apparatus is provided. The method includes detecting nuclear radiation by means of a movable detector during a detection period. The method further includes collecting detector data for image generation by means of an evaluation system of the image generating apparatus. The detector data include information about the detected radiation. The method further includes repeatedly determining at least one quality value from the collected detector data by means of the evaluation system during the detection period and outputting an instruction to a user for further moving the detector in dependence of the collected detector data and/or of the at least one determined quality value, wherein the instruction relates to at least a part of the remaining detection period.

According to a further embodiment a method for image generation by means of an image generating apparatus is provided. The method includes detecting radiation by means of a freely movable detector of the image generating apparatus during a detection period, and changing position and/or orientation of the detector during the detection period. The method further includes continuously collecting detector data for image generation by means of an evaluation system of the image generating apparatus during the detection period. The detector data include information about the detected radiation and information about the position and/or orientation of the detector. The method further includes determining at least one quality value from the collected detector data by means of the evaluation system.

According to a further embodiment, a method for image generation by means of an image generating apparatus is provided. The method includes detecting radiation by means of a movable detector of the image generating apparatus during a detection period. The method further includes changing the position and/or orientation of the detector during the detection period. The method further includes continuously collecting detector data for image generation by means of an evaluation system of the image generating apparatus during the detection period. The detector data include information about the detected radiation. The detector data further include information about the position and/or orientation of the detector. The method further includes determining at least one quality value from the collected detector data by means of the evaluation system.

According to a further embodiment, a method for image generation by means of an image generating apparatus is provided. The method includes detecting radiation by means of a detector of the image generating apparatus. The method further includes collecting detector data for image generation by means of an evaluation system of the image generating apparatus. The detector data include information about the detected radiation. The detector data further include information about the position and/or orientation of the detector. The method further includes determining an image generation rule by means of the evaluation system for image generation on the basis of the collected detector data, taking into account a detection model. The detection model takes into account a material property of a material influencing the detection and/or a constraint.

According to a further embodiment, a method for image generation by means of an image generating apparatus is provided. The method includes detecting radiation by means of a detector of the image generating apparatus. The method further includes collecting detector data of the detector for image generation by means of the evaluation system of the image generating apparatus. The method further includes registering the detector data with compatible data by means of the evaluation system.

According to a further embodiment, a method for image generation by means of an image generating apparatus is provided. The method includes detecting nuclear radiation by a movable detector of the image generating apparatus during a detection period. The method further includes collecting detector data for image generation by means of an evaluation system of the image generating apparatus. The detector data include information about the detected radiation. The method further includes determining an image generation rule by means of the evaluation system on the basis of the collected detector data. The method further includes repeatedly modifying the image generation rule on the basis of at least one quality value during the detection period.

Further features, aspects, and details which can be combined with embodiments described herein are disclosed in the dependent claims, the description and the drawings.

SHORT DESCRIPTION OF THE FIGURES

So that the above features can be better understood in detail, a more specific description is given with reference to embodiments of the invention. The appended drawings relate to embodiments of the invention and will be described shortly in the following.

DETAILED DESCRIPTION

Figure 1:
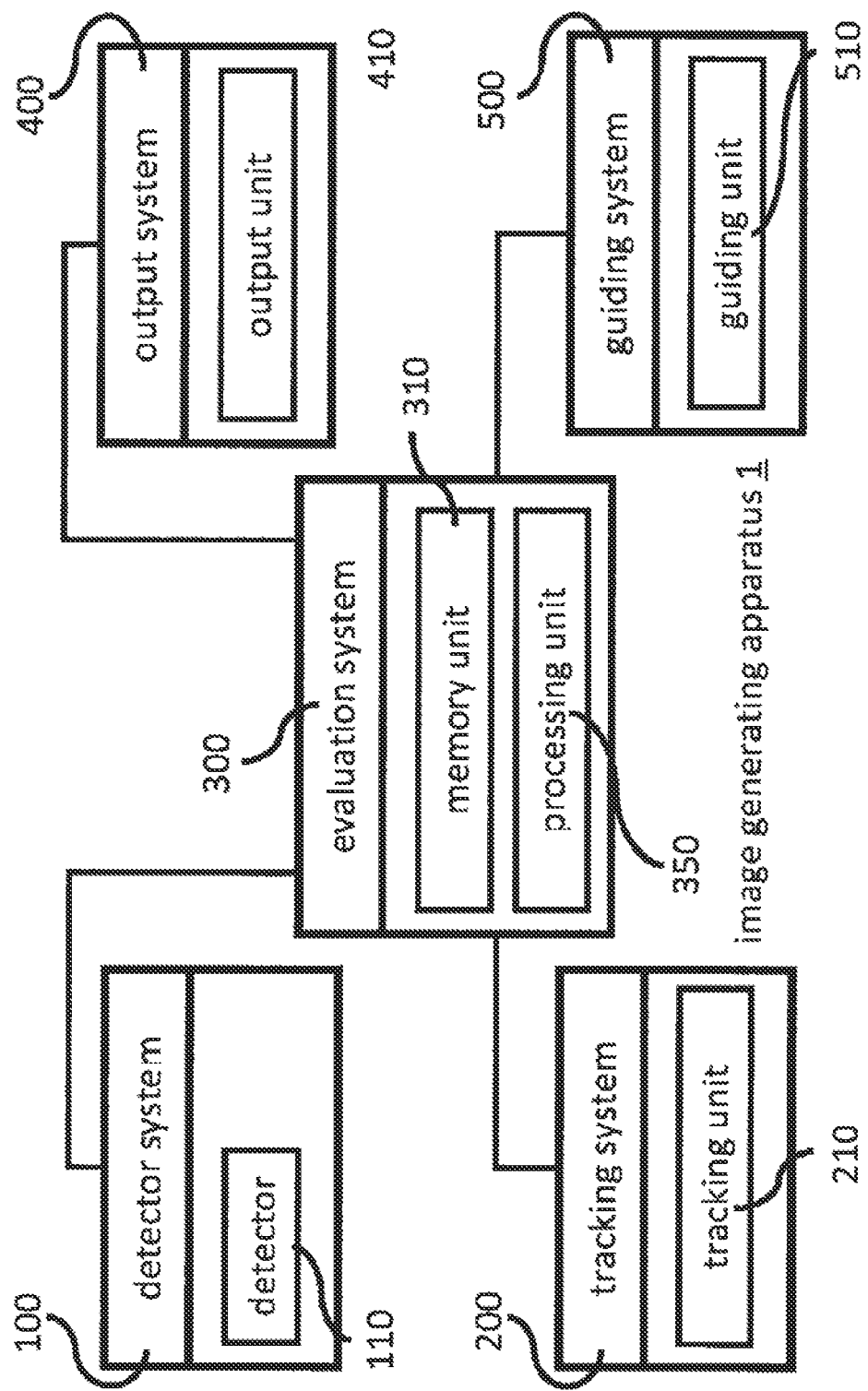
FIG. 1 shows a schematic arrangement of an image generating apparatus according to embodiments of the invention.

In the following detailed reference is made to various embodiments of the invention, of which some are exemplarily illustrated by the drawings. Each example is provided by means of explanation and for a better understanding of the invention and shall not be construed as limiting the invention. Thus, features which are described with respect to one embodiment, or are being illustrated with respect to one embodiment, can be combined with other embodiments to generate further embodiments. It is intended that such modifications and variations are encompassed.

In particular, embodiments of the invention are mostly described, for a better understanding, with respect to image generation for medical purposes. However, many of the embodiments can also be used for image generation in other fields.

Within the following description and in the drawings the same reference signs relate to the same or similar components. Generally, only the differences between individual embodiments are explicitly described.

The expression "detection period" used herein denotes a period between the beginning of a first detection process and the end of last detection process. The first and last detection process can be identical such that the detection period is a period during which a detection process continuously takes place. The first and last detection can also be different. In a detection period other processes can therefore lie. For example, such other processes can be data evaluation processes. The at least one detection process taking place in the detection period is carried out by the same detector, respectively detector system, on the same object. An example for a detection period is the period between the first measurement of nuclear radiation with a gamma probe on a patient and the last measurement, wherein for example after the last measurement a final image with the visualization of body functions can be generated. Between the first measurement and the last measurement there can also be one or several measurement pauses, for example for data evaluation or even for measurement on another object. A detection period would for example not be defined by a first measurement only on the back of a patient and by a further measurement only on the stomach of the patient.

Specifying that an action is carried out "during a detection period" (or more generally during any period) is not to be construed in the sense that the action needs to fill the full period. The action can also only take place during part of the detection period. The action can also be interrupted.

The expression "freely movable" is generally understood in that the position and/or orientation of an object which is freely movable can be changed substantially arbitrarily. For example, a detector which is handheld is a freely movable detector. Also, a detector which is mounted to a robot arm with sufficiently many degrees of freedom is freely movable, wherein the robot arm is for example controlled by a user. A detector which is movable along a rail is movable but not freely movable.

The expression "continuous" includes, when relating to an action such as "continuously collecting detector data", an ongoing or regularly repeated action. The temporal distances between the regular repetitions can in principally in principal be arbitrarily short, i.e. quasi-continuous. However, it is obvious for the skilled person that, for example, physical constraints can limit arbitrarily short distances. For example, detectors can have so-called "dead times" such that during such dead times no detection can take place. Consequently, also during e.g. a continuous collection of the detector data, a regular repetition of data collection within the collection process may not be possible within time intervals that are shorter than said dead times. The notion "continuous" includes, when used in relation to an action, also the repetition or the iterated repetition in arbitrarily short time intervals. Also arbitrarily selected time intervals can, in principle, be arbitrarily shortly following each other, and limitations as explained above apply analogously.

The "generation of an image" includes the generation of image data without the need for output of such image data to an output unit, for example a monitor.

FIG. 1 shows an image generating apparatus 1 according to embodiments of the invention. As shown in FIG. 1, the image generating apparatus 1 includes a detector system 100. The detector system 100 includes at least one detector 110. The image generating apparatus further includes an evaluation system 300. The evaluation system 300 includes at least one memory unit 310 and at least one processing unit 350. In some embodiments the detector system and the evaluation system are linked by a data exchange system 20. According to further embodiments, the image generating apparatus includes a tracking system 200 as shown in FIG. 1. The tracking system 200 includes at least one tracking unit 210. In further embodiments the image generating apparatus includes an output system 400. The output system includes at least one output unit 410. In some embodiments, the tracking system 200 and the output system 400 are connected to the evaluation system 300 by means of a data exchange system. In further embodiments the image generating apparatus includes a guiding system 500. The guiding system 500 includes at least one guiding unit 510. The guiding system can be connected to the evaluation system by means of a data exchange system. The individual systems are described in more detail in the following.

Detector System 100

According to embodiments of the invention, the detector system 100 includes a detector 110. In typical embodiments, the detector 110 is a radiation detector, typically a detector for nuclear radiation. According to some embodiments the detector is movable, according to specific embodiments even freely movable. In typical embodiments the detector is handheld. The detector can be a gamma radiation probe, a beta radiation probe, a Compton probe, a gamma radiation camera, a gamma radiation mini camera, a beta radiation camera or a Compton camera. The detector can also be a detector for optical radiation, a detector for infrared radiation, x-rays or a detector for other kinds of radiation or any other kind of detector.

Detector data can include information about the detected radiation. The detector data can be formatted to a certain degree but generally the association of single data sets to specific detection events or at least to a group of detection events should be possible. The detector data can also include position and/or orientation of the detector. Detector data can further include other data.

In some embodiments, the detector system 100 includes at least one further detector. The at least one further detector can be similar to the detector 110 or identical in built. The at least one further detector can also be of a different kind as compared to detector 110. The at least one further detector can, for example, be an ultrasonic probe, an x-ray detector, an optical camera, an optical microscope, a fluorescence camera, an auto-fluorescence camera, a magnetic resonance tomography detector, a positron emission tomography detector, short PET, a single photon emission computer tomography detector, short SPECT, or another kind of detector.

Figure 2:
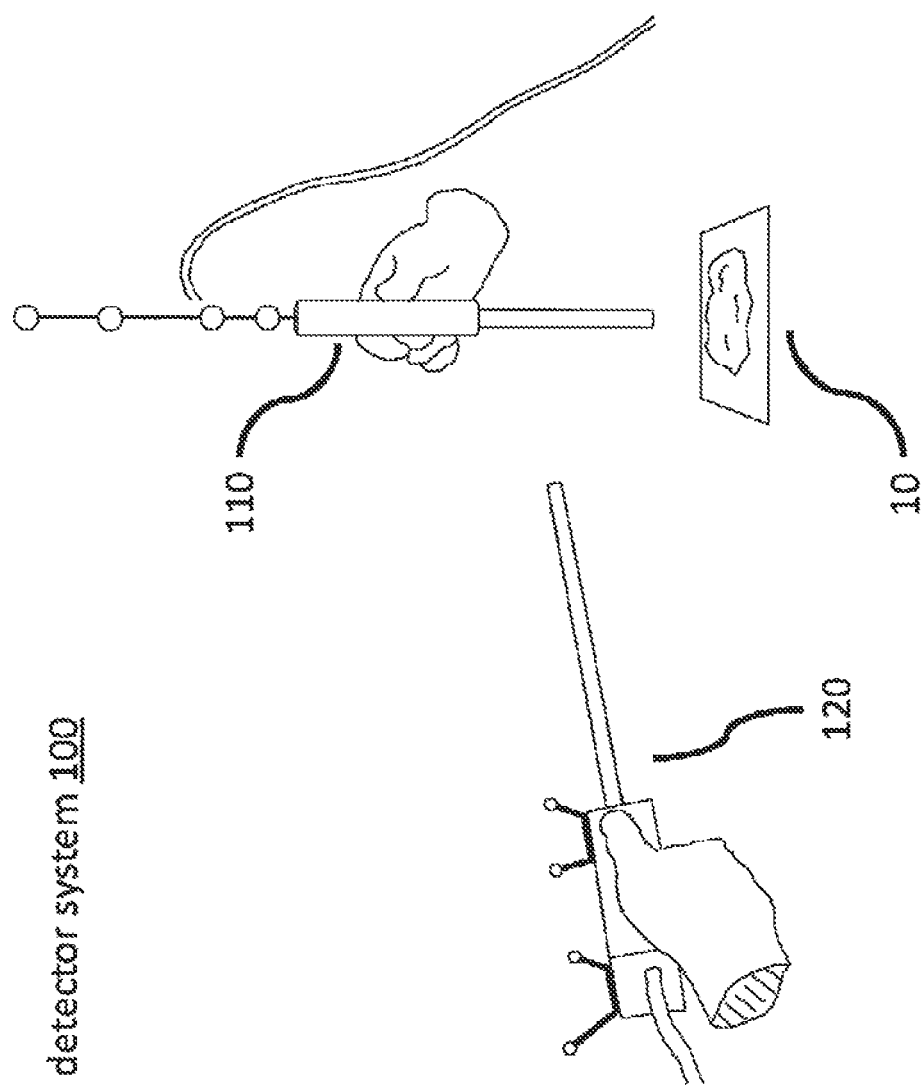
FIG. 2 shows a detector system of the image generating apparatus according to embodiments of the invention.

FIG. 2 shows a detector system 100 according to embodiments of the present invention. In FIG. 2, two detectors 110, 120 of the detector system 100 are shown: a probe 110 for detecting nuclear radiation and an optical camera 120. The nuclear radiation can for example be gamma, beta, Compton, x-ray, or alpha radiation. Further, a nuclear radiation source 10 that is to be detected is shown. A radiation source can generally be, here and in the following, a spatially distributed radiation source, i.e. a spatial radiation distribution. A radiation source can also be a substantially two dimensional radiation source, i.e. a radiation distribution that is substantially plane.

The detectors can be handheld as shown and be movable and orientable in the three spatial directions, i.e. freely movable. Further, the detectors 110, 120 each have a cable for power supply and for data exchange, e.g. with the evaluation system 300 shown in FIG. 1. Further, the detectors 110, 120 each have markings for tracking by the tracking system 200 shown in FIG. 3, as further described below with respect to FIG. 3. There can also be a tracking system 200 that works without markings.

Detector data, such as detector data with information about measured radiation, can be provided to the evaluation system 300 (see FIG. 1). In particular, the evaluation system 300 can collect the detector data.

Tracking System 200

According to some embodiments, the image generating apparatus includes a tracking system 200. According to some embodiments, the tracking system 200 includes a tracking unit 210. The tracking unit can be an optical, electromagnetic, mechanical, robot-based, radio wave-based, sound wave-based, goniometer-based, potentiometer-based, gyroscope-based, acceleration sensor-based, radiation-based, or x-ray-based detection unit, or an infrared or white light detection unit or another kind of detection or tracking unit. According to further embodiments, the tracking system 200 includes a further tracking unit 220 or further tracking units. The tracking unit 220 or the further tracking units can be tracking units as the ones listed above or can be other tracking units. To guarantee feasibility or reliability of the tracking system, some embodiments have at least two, at least three or at least four tracking units.

Figure 3:
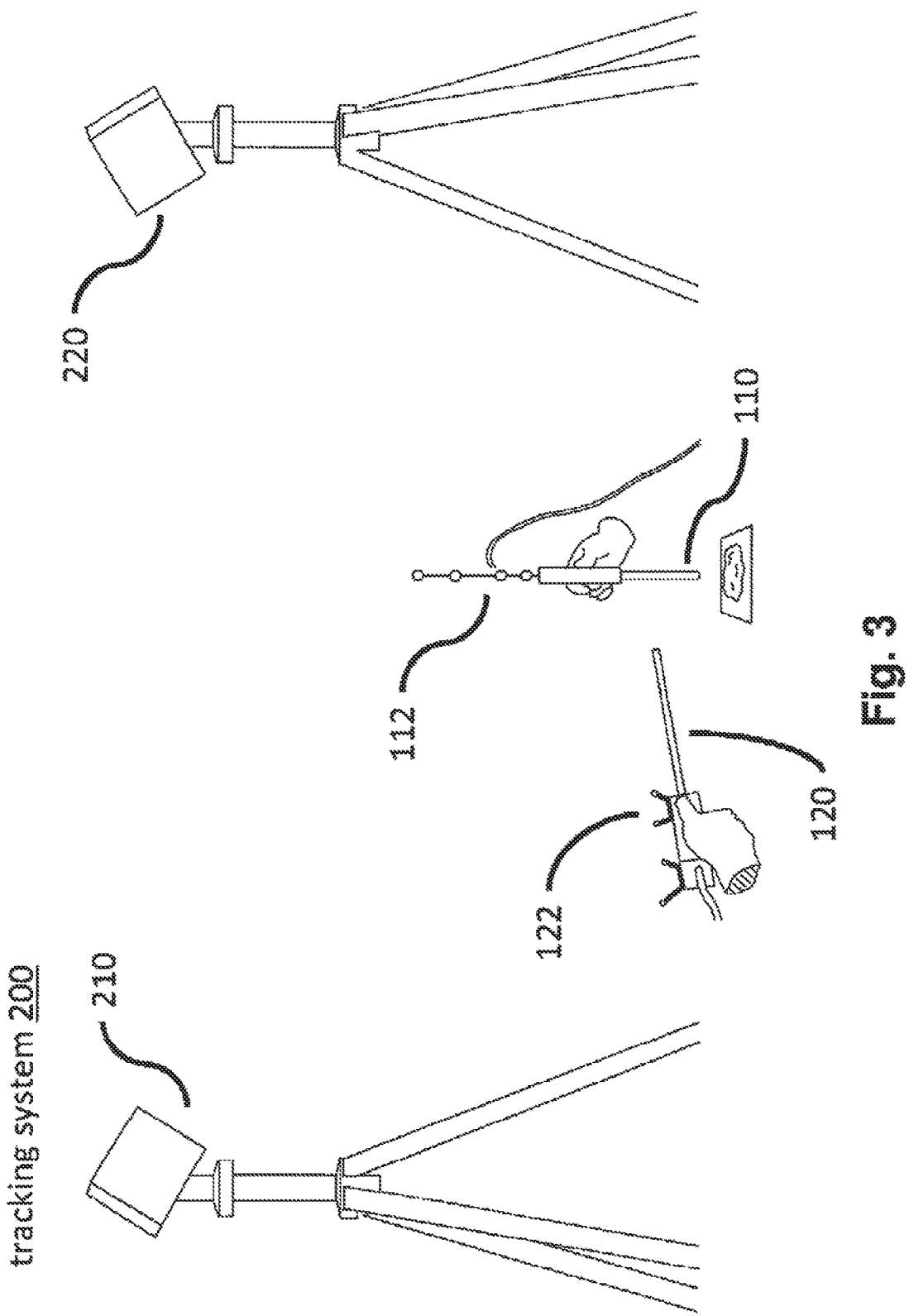
FIG. 3 shows a detection system of the image generating apparatus according to embodiments of the invention.
Figure 4:
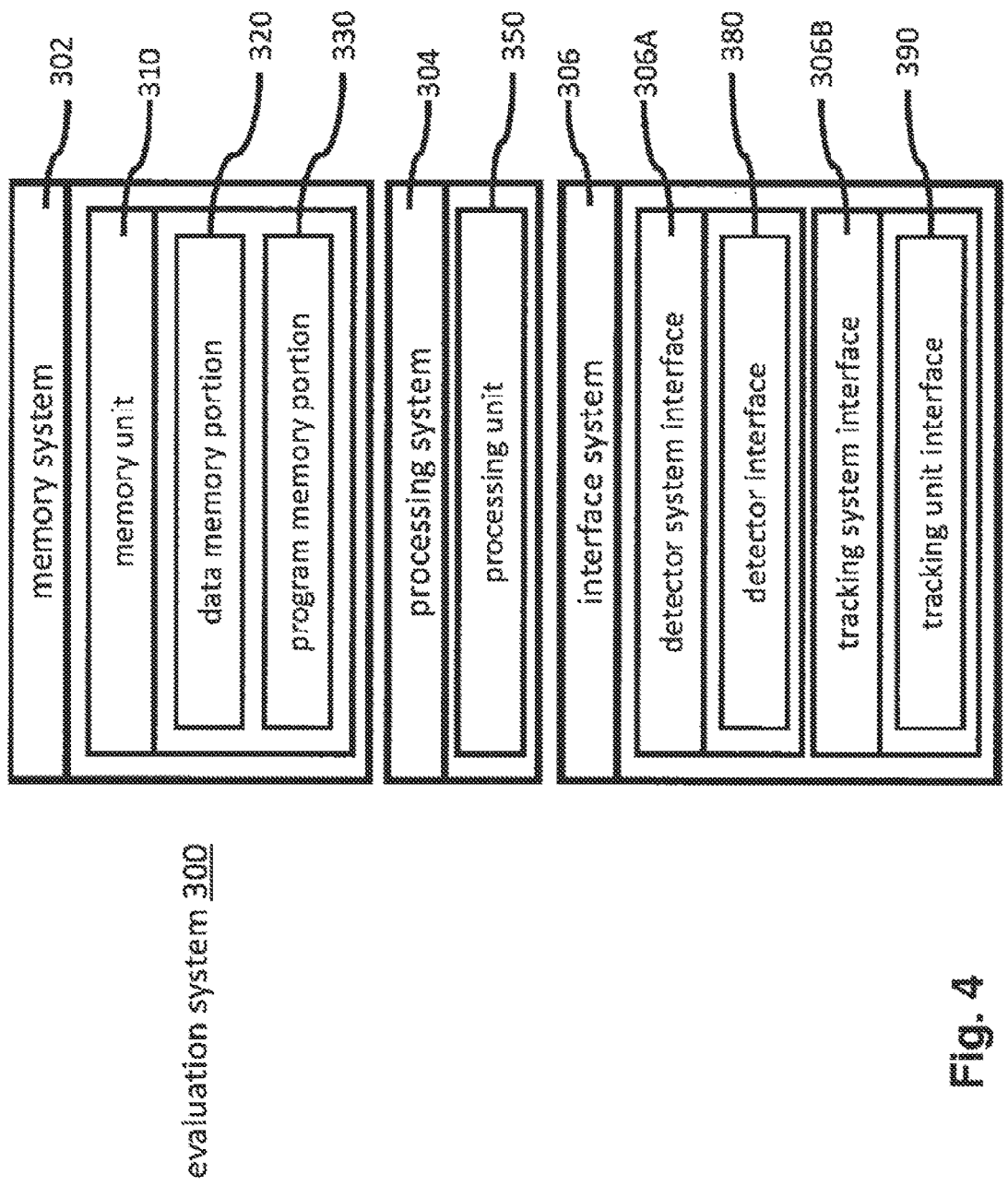
FIG. 4 shows a schematic arrangement of an evaluation system of the image generating apparatus according to embodiments of the invention.

FIG. 3 shows a tracking system 200 according to typical embodiments of the present invention. FIG. 3 shows two optical tracking units 210 and 220. The optical tracking units 210 and 220 detect markings 112 on the probe of nuclear radiation 110 and markings 122 on the optical camera 120. The optical tracking units 210 and 220 generate, by detecting the markings 112 and 122, data with information about the position and/or orientation of the probe 110 and the camera 120. In the example shown in FIG. 3, the optical tracking units 210 and 220 are exactly calibrated, and the position and orientation of probe 110 and of the camera 120 is being determined by detecting the position of the markings 112, and 122 respectively, by means of known triangulation methods.

Data of the tracking systems, such as detector data with information about the position and orientation, can be provided to the evaluation system 300. In particular, the evaluation system 300 can collect such and other detector data.

Evaluation System 300

According to embodiments of the present invention, the evaluation system 300 includes a memory system 302 with a memory unit 310. The memory unit 310 can for example be a computer hard drive or another mass storage device, or can be of a different kind. According to embodiments of the invention, the storage unit 310 includes a data storage portion 320. The data storage portion 320 can for example be used for storing detector data. The data storage portion 320 can also be used for storing other data. According to embodiments, the storage unit 310 includes a program storage portion 330. The program storage portion 330 as well as further program storage portions according to further embodiments will be described further below. The data storage unit 310 can include further data storage portions and further program storage portions. The different storage portions need not physically or in a memory-technical sense form a unit; different portions are rather distinguished only with respect to the nature of the data stored or to be stored therein. The memory system 302 can include further memory units. The further memory units can be similar to memory unit 410 or of a different kind.

According to further embodiments, the evaluation system 300 includes a processing system 304. The processing system 304 includes a processing unit 350 according to some embodiments. The processing unit 350 can for example be the computing part of a computer, for example a processor. According to further embodiments the processing system 304 includes further processing units, which can be similar to the processing unit 350 or be of a different kind. In particular, at least one processing unit and at least one memory unit can be integrated in special devices, such as commercially available computers.

According to further embodiments, the evaluation system includes an interface system 306. In some embodiments the interface system 306 includes a detector system interface 306a with a detector interface 380 for data exchange with a detector, for example with the detector 110. In further embodiments the interface system 306 includes a tracking system interface 306b with a tracking unit interface 390 for data exchange with a tracking system (for example, the tracking system 200 of FIG. 3). An interface system 306 or parts thereof can also be integrated in special devices, such as commercially available computers. In some embodiments, the evaluation system communicates with other partial systems of the image generating apparatus via such interface systems by means of a data exchange system.

Figure 5:
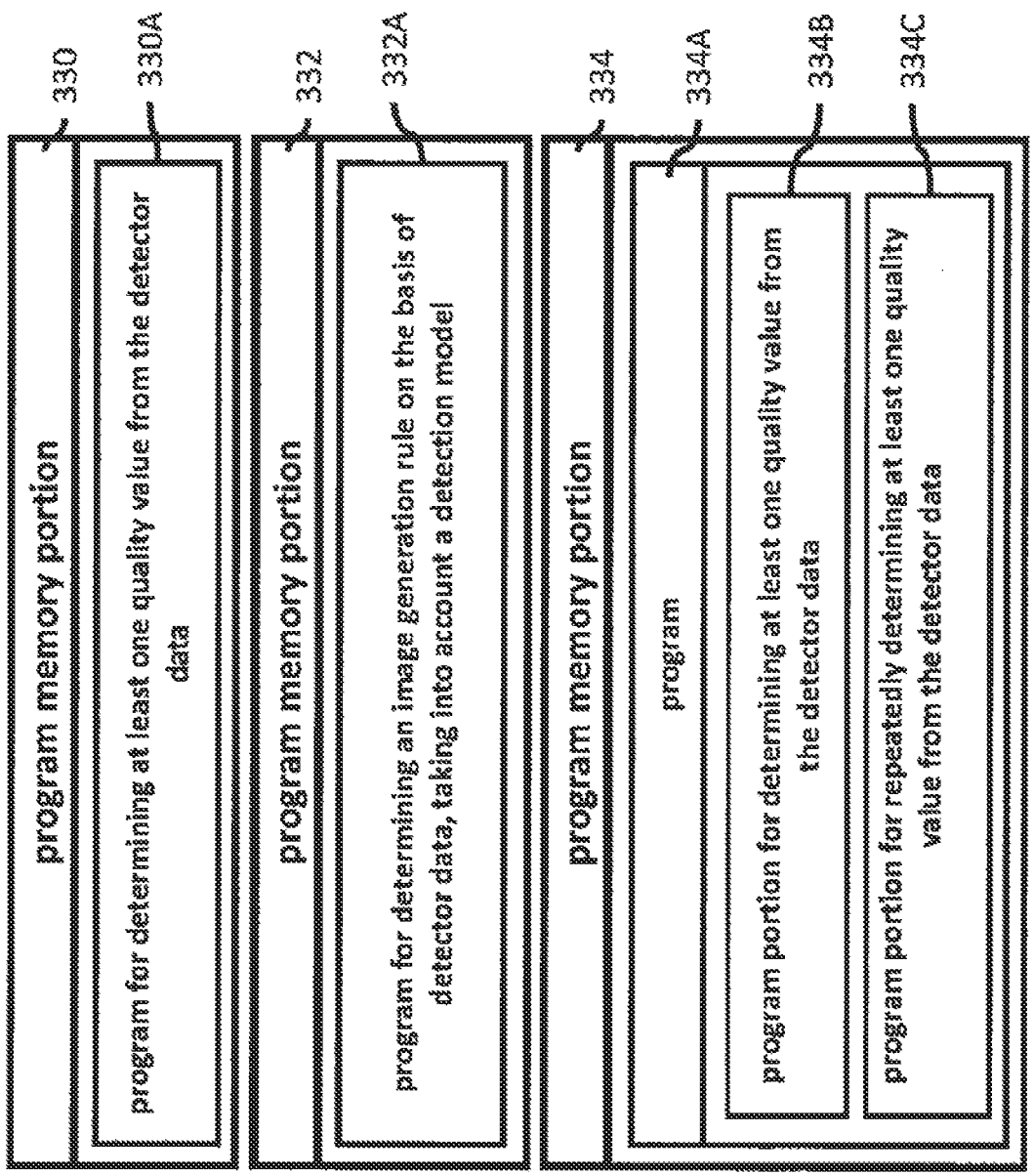
FIG. 5 shows a schematic arrangement of program memory portions of the evaluation system according to embodiments of the invention.

In further embodiments of the invention, the program memory portion 330 includes a program. As shown in FIG. 5, the program can for example be a program 330 for determining at least one quality value on the basis of detector data. In other embodiments, a memory unit includes further program memory portions, for example further program memory portions 332 and 334 with program 332a for determining an image generation rule on the basis of detector data while taking into account a detection model and respectively with a program 334a. Program 334a includes program part 334b for determining at least one quality value on the basis of detector data and program part 334*c* for repeatedly determining at least one quality value on the basis of detector data.

In particular, programs, which for example carry out similar functions, can also be formed as program parts of a single program, as for example described above for program 334*a*. The same is also true for functionally different programs. In both cases, the first program portion with a first program and a second program portion with a second program are identical, and the first and second program are considered as parts of a single program.

In further embodiments, in which a first program portion with a first program and a second program portion with a second program are provided, the first program portion can be identical to the second program portion as well as the first program to the second.

Output System 400

Figure 6:
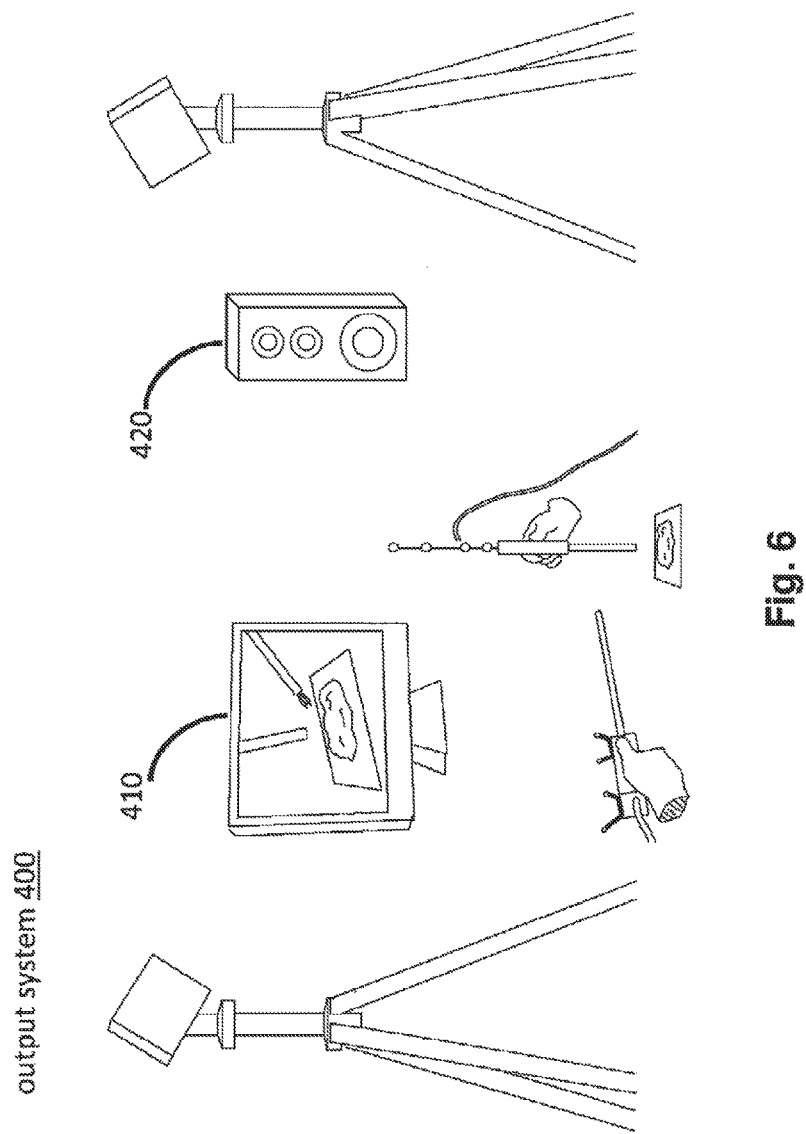
FIG. 6 shows an output system of the image generating apparatus according to embodiments of the invention.

With reference to FIG. 6, the image generating apparatus includes an output system 400 according to further embodiments. The output system 400 includes an output unit 410 according to some embodiments. The output unit 410 can be a visual, acoustical or haptic output unit or a combination form thereof In some embodiments, the output unit 410 is an output unit for displaying images or an instruction to a user. A user is usually a human being. Alternatively, a user can also be a different living being or an inanimate object, for example a machine.

In further embodiments, the output system 400 includes further output units. These can be of similar kind as the output unit 410 or of a different kind.

Output units according to embodiments of the present invention can display reality, display a virtual reality or display an augmented reality. An output unit of an augmented reality can for example combine a real image with virtual images.

According to embodiments of the invention, an output unit can, among others, be one of the following: monitor, optically transparent monitor, stereo monitor, head-mounted stereo displays, acoustical frequency-coded feedback systems, acoustical pulse-coded feedback systems, force-feedback joysticks or force-torque-feedback joysticks or other kinds of visual, acoustical and/or haptic output units or combinations thereof.

FIG. 6 shows an output unit 410 according to embodiments of the present invention. In FIG. 6, the output unit 410 is an optical output unit, in particular a monitor. FIG. 6 shows further an acoustical output unit 420. In FIG. 6, the acoustical output unit is a loudspeaker.

Figure 7:
FIG. 7 shows a further output system of the image generating apparatus according to embodiments of the invention.

FIG. 7 shows a further output unit 430 in form of a head-mounted visual display.

Guiding System 500

Figure 8:
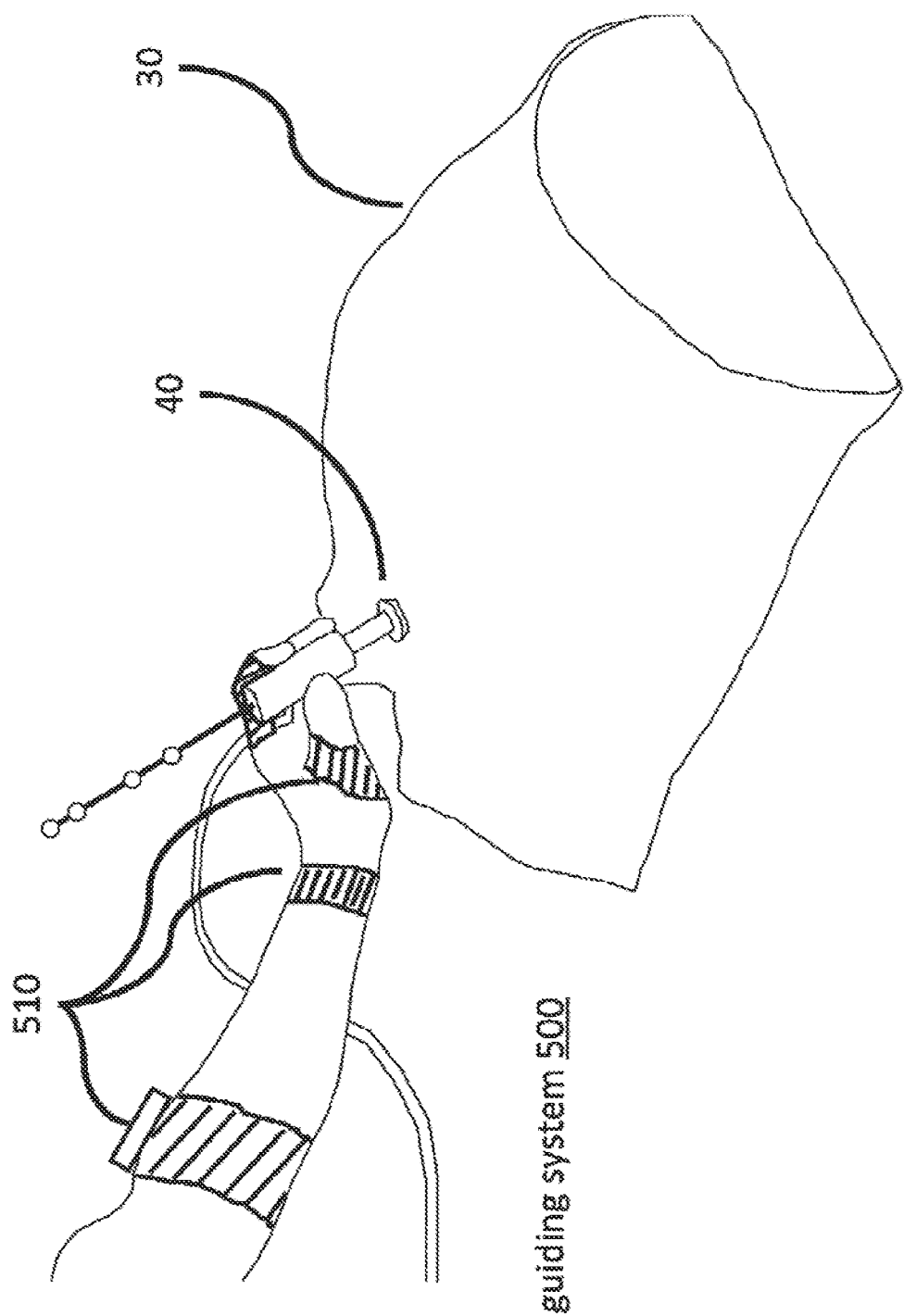
FIG. 8 shows a guiding system of the image generating apparatus according to embodiments of the invention.

In further embodiments, the image generating apparatus includes a guiding system 500, as for example shown in FIG. 8. According to some embodiments, the guidance system 500 includes a guiding unit 510. A guiding unit 510 can for example guide an object by means of a robot arm. The guiding unit 510 can also guide a user. Guiding can also be robot-based or else can rely upon optical, acoustical or haptic signals or on combinations thereof The guiding unit 510 shown in FIG. 8 guides the user by haptic signals. In FIG. 8, the guiding unit 510 serves for better guiding a surgical instrument 40 during surgery on a body 30. The guiding unit may for example provide a resistance, be it by mechanical hindrance or by stimulation of the muscles by means of electrical pulses.

The guiding unit 510, or further guiding units, can also be formed by output units of the output system if the guidance of the user is effected by a corresponding output. The guiding system 500 can therefore be identical with the output system 400.

In further embodiments, the image generating apparatus includes a data exchange system. As shown in FIG. 1, the data exchange system serves for exchanging data between systems of the image generating apparatus, for example for exchange of data between detector system and evaluation system, between tracking system and evaluation system, between output system and evaluation system, or between guiding system and evaluation system (as shown in FIG. 1 by means of corresponding connection lines). The data exchange system can rely upon interfaces such as the detector interface 380 or the tracking system interface 390, according to some embodiments. Generally, the exchange of data can take place by a connection of the systems by means of cables or else wireless or in any other way.

Figure 9:
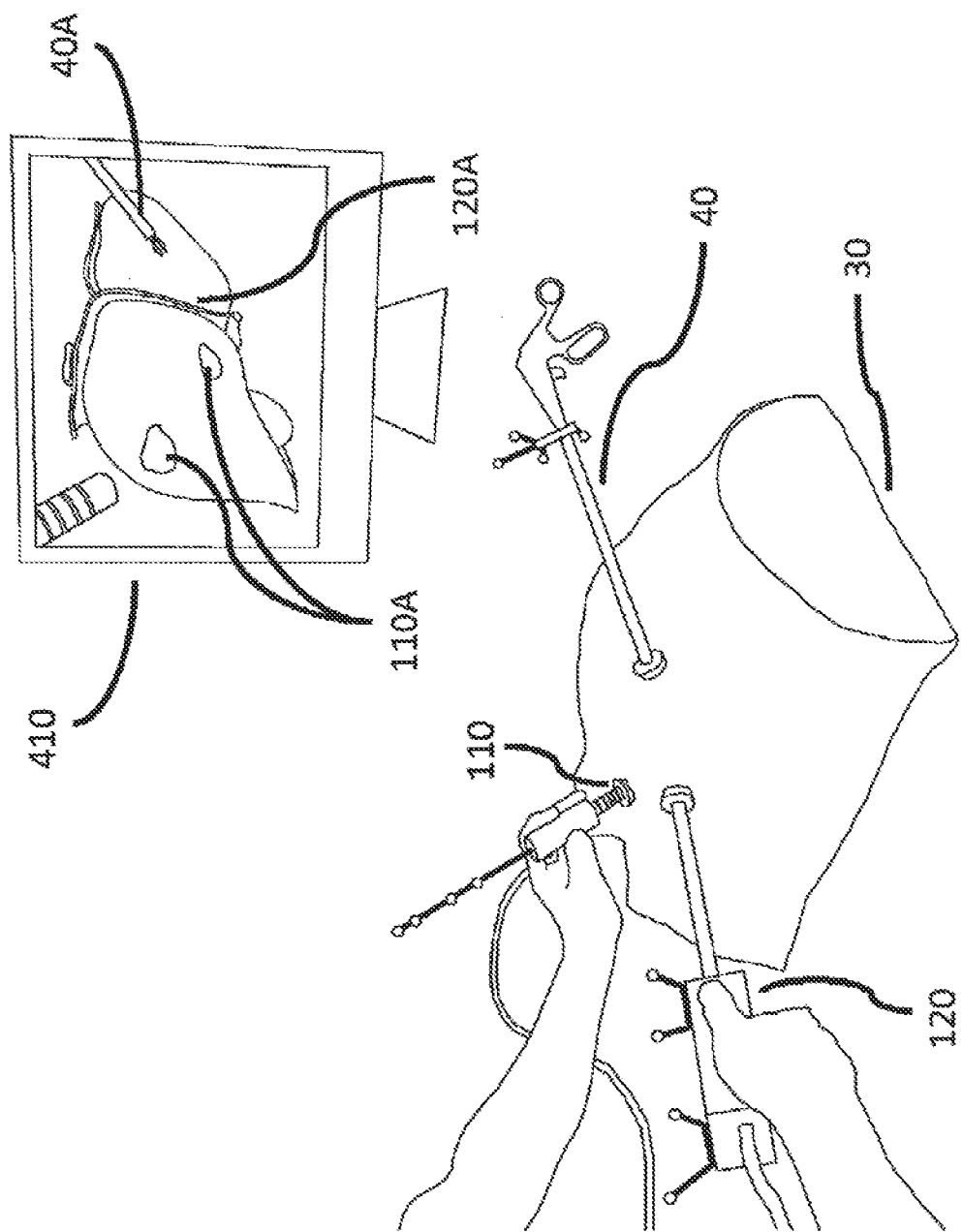
FIG. 9 shows an image generating apparatus according to embodiments of the invention at use in the medical field.

FIG. 9 shows, according to embodiments of the invention, a body part of a human or other living being, into which radioactive substances have been injected, so-called tracers, which accumulate in certain preferred regions and are stuck there. The regions or spatial areas in which the radioactive substances are accumulated, respectively are stuck, can be regarded as closed regions which include a source of nuclear radiation.

FIG. 9 further shows a detector for nuclear radiation 110. The detector 110 measures the nuclear radiation that emerges from the source within the body. Further, FIG. 9 shows a laparoscope 120 which gathers data for generating an optical image of the interior of the body. The data gathered by the detector for nuclear radiation 110 and the laparoscope 120 are collected in the evaluation system (not shown) and are processed. Further, the position and/or orientations of the two detectors are tracked via markings 112 and 122, and corresponding data is collected by the evaluation system. From all these data, the evaluation system generates, with the help of an image generation rule, an optical image of the interior of the body based on data of the laparoscope as well as a functional image, that visualizes body functions such as metabolism, based on the data of the detector for nuclear radiation. The image can in particular be three dimensional.

On an output unit 410, the optical anatomic image and the functional image are overlaid and, for example, displayed three dimensionally. The overlay is generated on the basis of a registration of the optical image with the anatomic image by means of the evaluation system.

Further, FIG. 9 shows a surgical instrument 40 the position and/or orientation of which are also tracked. The gathered data of the surgical instrument are also processed by the evaluation system. In this way, an image of the surgical instruments and of their location in the interior of the body can be determined by the evaluation unit. This image can also be registered with the anatomic and optical image and be displayed on the output unit 410. If, in particular, the functional image is high quality and up-to-date and if the registration with the optical image and the instrument image is good, the output of the registered images on the output unit enables a surgeon to precisely control the surgery.

The images of known image generating apparatuses and of corresponding methods for image generation are, however, oftentimes images used in surgery, but which are not up-to-date.

This applies for example to pre-operative images, since the taking of which the tissue and its functions may already have undergone change. If intra-operative images are used, problems oftentimes result in particular when using movable detectors, because then known evaluation systems are not capable of guaranteeing a high quality image. To enhance image generation there is a need of quality control, in particular a quality control already during the gathering of detector data. Such quality control can also be a continuous quality control. Further, for enhancing image generation, an enhanced data set is desirable, which can be insured by giving instructions for detection. In particular, with movable or even handheld detectors, the gathering of detector data which can in principle take place at any moment and with any arbitrary position and/or orientation of the detector, poses a challenge. For enhancing image generation, it is further desirable to use existing information, for example about anatomic facts, detector properties, other material properties which may influence the detection, or about constraints. Also an enhancement of registration of the images can contribute to enhance image generation. Changing an enhancing the imaging rule already during the detection period can also enhance image generation overall.

According to embodiments of the invention, means for enhancing image generation are provided.

Collecting Detector Data

According to embodiments of the present invention, detector data are collected by the evaluation system. Therein, position and/or orientation of the detector can have been tracked by a tracking system. The detector data include information about the detected nuclear radiation, according to some embodiments. In further embodiments, the detector data include information about the position and/or orientation of the detector. For example, data with information about the detected radiation can be synchronized with data about the position and/or orientation of the detector and be collected in synchronized form. With respect to synchronization of data, see WO 2007/131561, in particular page 3, lines 1 to 6 and lines 27 to 32, and page 6, lines 22 to 30, in corporate herein by reference. The WO 2007/131561 is further included herein by reference in its entirety. In further embodiments, the detector data are stored in the evaluation system.

In further embodiments, a detector detects radiation during a detection period. This radiation can be radioactive, respectively nuclear radiation. Nuclear radiation is also to be understood as radiation which is indirectly generated by radioactive decays, for example ionization radiation of an alpha particle. Embodiments of the invention in which the detector measures nuclear radiation hence also include detecting of such secondary radiation.

Image Generation and Image Generation Rule

In further embodiments, the evaluation system generates an image from the detector data by means of an image generation rule. In typical embodiments, this image is an image of the radiation distribution and thus of the radiation sources in a spatial region.

According to further embodiments, the image generation rule is a linear rule. Therein, an imaging matrix H, also called system matrix, is typically applied to a vector $f=(f_1, f_2, \ldots, f_N)$. The vector f contains image information. Typically, for visualizing an image of a spatial region, this spatial region is divided into image elements (voxel). Each index $i=1, 2, \ldots, N$ of the vector f is then associated with a particular image element. Information elements with respect to these image elements (for example the intensity of radiation in the corresponding image element) form the entries $f_i$ of the vector f to a corresponding index i.

The detector data are also collected in a vector $g=(g_1, g_2, \ldots)$. Each index $k=1, M$ is thereby associated to a measurement (or an averaged series of measurements, see below) of a detector, and the entry $g_k$ contains the result of the intensity of radiation measured during this measurement.

The entries $H_{ki}$ of the imaging matrix H model the influence of a normalized radiation source at the position belonging to the index i onto the $k^{th}$ measurement. The imaging matrix H contains, in its entries $H_{ki}$, information about positions and orientations of the detector for nuclear radiation. As the different contributions linearly superpose, a result of the measurement with a radiation distribution $f_i$ is to be expected which is approximately given by the vector $g\_predicted_k=\Sigma_i H_{ki}f_i$. In matrix notation (with "*" as matrix product):

$$g\_predicted = H*f$$

Such a vector g_predicted can be compared to a vector g_measured which contains the actual detector data with information about the detected radiation. In this comparison, different measurement errors, for example contributions of external radiation sources, imperfections of the detector, statistical errors, etc. are to be taken into account.

The image generation can now be described in a way that a vector f with data information regarding the radiation distribution in a spatial region shall be found that best corresponds to the actually measured data about the nuclear radiation. For this, a conceptual ansatz is the minimization of the distance $$|H*f-g\_measured|,$$

over all estimated radiation distributions the image information of which is coded into a respective vector f. Therein, |•| denotes a suitable distance norm. In typical embodiments, |•| is computed as the $L_2$ norm. This minimization can also be implemented as an iterative process. The involved minimization process can be carried out for example by algebraic reconstruction techniques, maximum likelihood expectation value maximization, pseudo inversion by means of singular value decomposition, Gauss-Seidel inversion, successive over-relaxation, Jacobi inversion, multiplicative algebraic reconstruction techniques, simultaneous iterative reconstruction techniques or by other techniques. Also, regularization methods such as Tikhonov regularization, total variation regularization and other regularizations can be used. In light of this, the image generation rule is defined, in the first line, by the matrix H. But, also the algorithm to be used for solving the minimization problem as well as the starting vector to be used in an iterative solution are part of the image generation rule.

In further embodiments, the image generation rule is non-linear. Also for such a non-linear image generation rules, analogous methods can be applied.

Detection Models

According to embodiments, image generation rules, in particular the matrix H described above can be generated or enhanced on the basis of at least one detection model. Detection models can be changed or adapted, in particular on the basis of new detector data. According to some embodiments, detection models can be enhanced or be continuously enhanced. Enhanced or continuously enhanced detection models can be used for enhancing an image generation rule.

With a linear image generation rule according to embodiments of the present invention the entries of the imaging matrix can be calculated with the help of detection models. Such detection models can be generated by algebraic, analytic, numeric, or statistical methods, or on the basis of measurement data or by combinations thereof In some embodiments, detection models are generated by measurements on a radioactive point source which is positioned differently and the radiation of which is measured from different positions and orientations. By such measurements or by suitable detection models, information is gained about for example at least one material property of at least one material, or such information is used. In the case of image generation for medical purposes, material properties of materials distributed in space can be determined, such as operation table, instruments, but also the patient himself.

Material properties include the attenuation between source and detector, the scattering between source and detector, the material properties of materials between source and detector, the attenuation by a detector shield or the scattering by a detector shield, the attenuation in the detector itself and the scattering in the detector itself.

Further, analytic, algebraic, numerical, or statistical models, or models that are combinations thereof, can also take into account constraints besides material properties. Examples for constraints are the relative solid angle between a detector and a source area of radiation, the dimensions of the detector or the absence of material or matter. Constraints allow to exclude certain image vectors f from the start, and to thereby obtain better results of the optimization problems described above.

Figure 10:
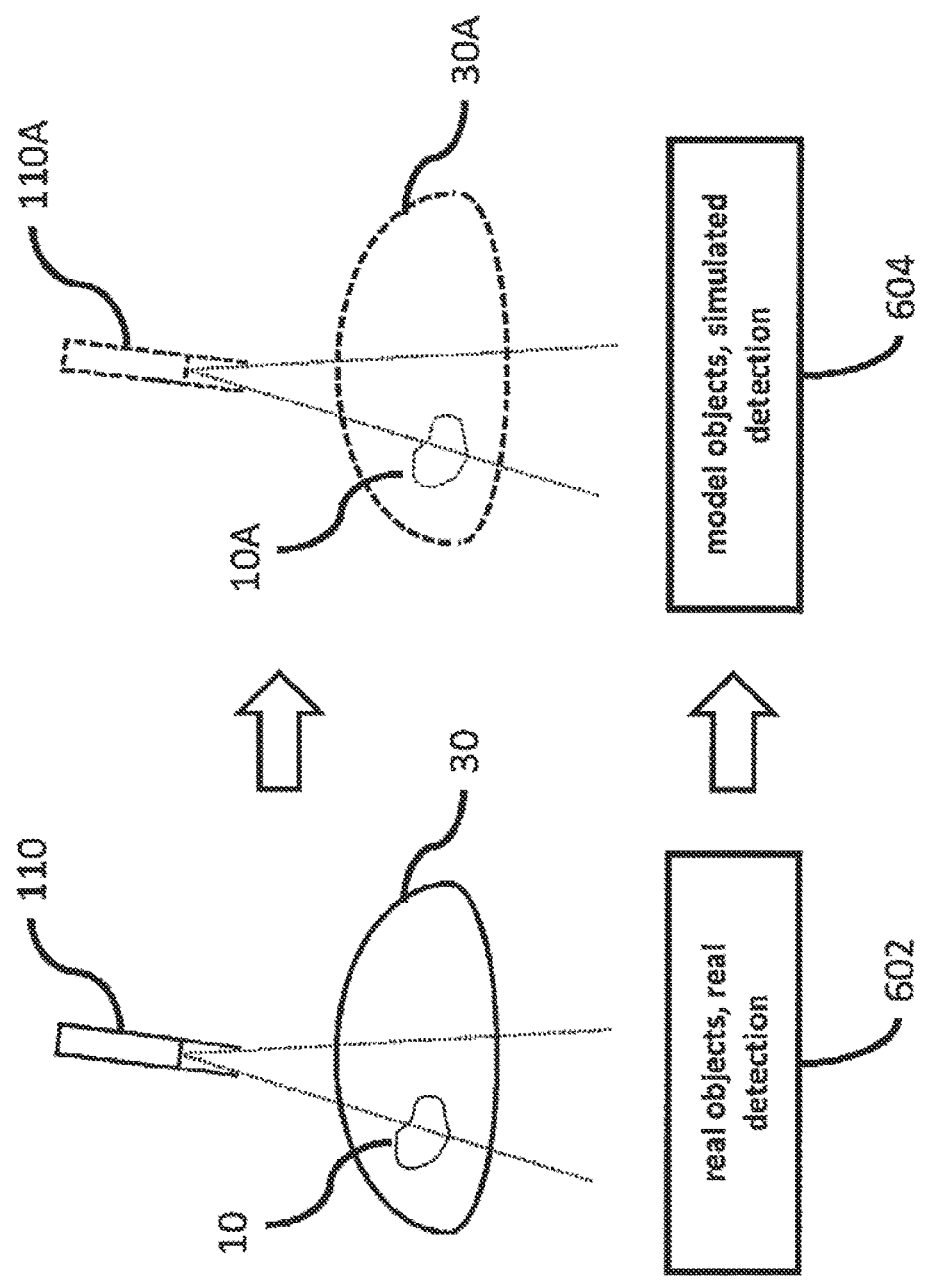
FIG. 10 shows the generation of a detection model according to embodiments of the invention.

FIG. 10 schematically shows the mapping of real objects and of a real detection process onto a detection model and a simulated detection process. According to embodiments of the invention, real objects such as a detector 110, a body 30 and a source of radiation 10 within the body are mapped to data of a detection model. Therein, data with respect to a detector describe a virtual detector 110a, data with respect to the body describe a virtual body 30a, and data with respect to the radiation source describe a virtual radiation source 10a.

Figure 11:
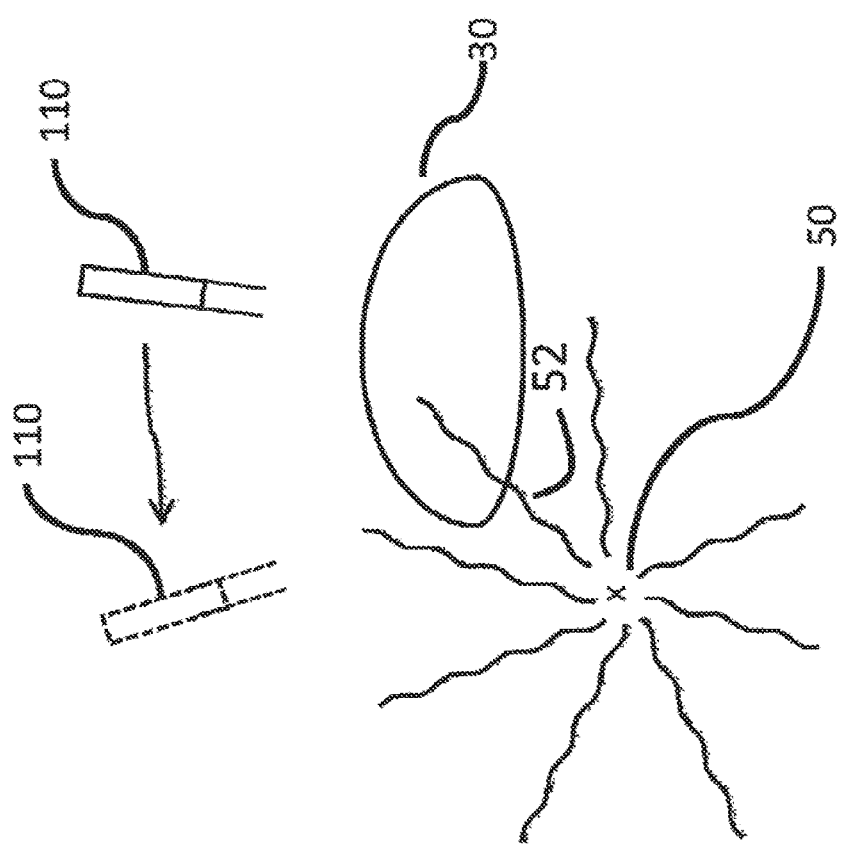
FIG. 11 shows the generation of a detection model via measurements according to embodiments of the invention.

FIG. 11 illustrates the determination of a detection model on the basis of measurements. A radioactive point source 50 emits nuclear radiation 52 in all spatial directions. A detector 110 measures the radiation source 50 at different positions and with different orientations (second position/orientation is depicted with dashed lines), whereby information about material properties are gained. Material properties can for example include those of the body 30. From the measurement data, a detection model can be determined The detection model can take into account the information of the measurement data and further information, such as for example the detector geometry.

According to embodiments of the present invention, a method for image generation by means of an image generating apparatus is provided. The method includes detecting radiation by means of a detector of the image generating apparatus. The radiation may be nuclear radiation. Detecting can take place during a detection period. The method further includes collecting detector data for image generation by means of an evaluation system of the image generating apparatus. In typical embodiments, the detector data include information about the detected radiation. In further typical embodiments, the detector data include information about the position and/or orientation of the detector. The method further includes determining an image generation rule by means of the evaluation system for image generation on the basis of the collected detector data, taking into account a detection model. In typical embodiments, the detection model takes into account a material property of a material influencing the detection and/or of a constraint.

According to further embodiments, the detector is movable. According to further embodiments, the detector is freely movable. In further embodiments, the detector is handheld. In typical embodiments, the method includes again, repeatedly, or continuously collecting detector data for image generation by means of the evaluation system of the image generating apparatus, typically during a detection period.

In some embodiments, the method further includes determining at least one quality value from the collected detector data by means of the evaluation system. In further embodiments, the method includes again or repeatedly determining at least one quality value form the collected detector data by means of the evaluation system. Typically, determining, again determining, repeatedly determining, or continuously determining takes place during a detection period.

In particular, the detection model according to embodiments of the invention can be generated algebraically, analytically, numerically, statistically, or on the basis of measurement data, or by combinations thereof.

In further embodiments, the detection model takes into account at least one further material property and/or at least one further constraint. Material properties can for example influence the detection model because of the following effects: attenuation of radiation, scattering of radiation, refraction of radiation, diffraction of radiation, influence of electromagnetic fields, influence of background radiation, signal noise, or influence of errors in the measurement values of the detector as well as in measurements of position and/or orientation of the detector. Embodiments of the invention can include detection models that take into account these and other effects.

Methods for image generation according to embodiments of the invention can also take into account at least one constraint, wherein the constraints can for example be the relative solid angle between the detector and the source region of radiation, the dimensions of the detector or the absence of material.

According to further embodiments, an image generating apparatus for image generation is provided. The image generating apparatus includes a detector for detection of radiation. The detector can be a movable detector. The detector can be a freely movable detector. The detector can be a handheld detector. The radiation can be nuclear radiation. The image generating apparatus further includes an evaluation system. The evaluation system includes an interface system for transmitting detector data for image generation to the evaluation system. Typically, detector data include data with information about the detected radiation. Typically, the detector data also include data with information about the position and/or orientation of the detector for image generation. The evaluation system further includes a data memory portion for storing detector data. The evaluation system further includes a program memory portion with a program for determining an image generation rule for image generation on the basis of the collected detector data, taking into account a detection model. In typical embodiments, the detection model takes into account at least one material property of at least one material influencing the detection and/or at least one constraint.

In further embodiments, the interface system is an interface system for transmitting detector data to the evaluation system. Therein, the detector data typically include information about the detected radiation. Typically, the data also include information about the position and/or orientation of the detector. According to further embodiments, the interface system is an interface system for continuously transmitting detector data to the evaluation system for image generation. The detector data can again include information about the detected radiation and/or information about the position and/or orientation of the detector. Typically, the transmission is a transmission during the detection period.

According to further embodiments, the detection model takes into account an attenuation of radiation, a scattering of radiation, a refraction of radiation, a diffraction of radiation, the influence of electromagnetic fields, the influence of background noise, a signal noise, the influence of errors in the measurement data of the detector and in the measurement of position and/or orientation of the detector or further effects. In yet further embodiments, the detection model takes into account constraints such as the relative solid angle between the detector and a source region of radiation, the dimension of the detector or the absence of a material or combination of these constraints.

According to further embodiments image generation rules are modified. In particular, with linear image generation rules, the entries of the imaging matrix or system matrix are modified. In typical embodiments, the system matrix is modified as soon as further measurement data are available. Specifically, the minimization of the norm of the difference between H applied to f and a g_measured can be minimized again as soon as further measurement data are available. Consequently, embodiments typically include a continuous modification of the image generation rule. Also, detection models can continuously be adapted and enhanced.

Registration

According to further embodiments, detector data are registered with compatible data. In some embodiments, a compatible data are gained by an imaging rule from the given image. Such an image can for example be an anatomical or body-functional image that was taken beforehand (pre-operatively taken). In the case of a linear imaging rule, this can be described by an imaging matrix H as described above. The matrix H can depend on a location vector T, in which information about the relative location and/or orientation between the detector and the source of radiation is included. Therein, T can describe a relative location in the sense of a rigid registration or in the sense of a deformable registration. The matrix H(T), i.e. dependent on T, is applied to a vector $f_{image}$ as described above to obtain a vector with (theoretical) detector data $g=H(T)*f_{image}$ associated with the image.

The information contained in g represents predicted or virtual or simulated detector data which are called simulation detector data. As before, the vector $g_{measured}$ contains information about detected radiation. The format (i.e. the structure of the vector g) of the simulation detector data is compatible with the measured detector data $g_{measured}$. A registration of detector data with such compatible data takes place, according to some embodiments of the invention, in that the distance $|H(T)*f_{image}-g_{measured}|$ is minimized, i.e. between g and $g_{measured}$. The distance $|\cdot|$ can for example be given by the $L_2$ norm. The minimization takes place overall location vectors T to obtain, as a results of the minimization, an optimal location vector T. By using this optimal location vector T, an image vector is associated to the measured detector data by the matrix H(T), the image vector being compatible with the image vector of the given image and being registered.

In typical embodiments the minimization is carry out by algorithms such as the best-neighbour ansatz, a simplex-optimizer, the Levenberg-Marquardt algorithm, the steepest gradient decent, the conjugate gradient decent, or others.

The registration not only can take place by comparing the detector data g as described above, but also by direct comparison of the image data f gained from the detector data with a given image. This comparison can be carried out by an image comparison with the methods described above with respect to g, or else by a comparison of single marking points designated for this purpose. Also, other registration methods are possible.

The image comparison described above further allows obtaining an estimation of the quality of the collected data (as deviation between the image data gained from the detector data and the given image).

Data can be indirectly registered with compatible data also. Indirect registration is to be understood as a registration of a first data set with a third data set by means of a second data set. To this end, the first data set is registered with a second data set, for example as described above. Then the second data set is registered with a third data set. By using this registration the first data set is finally registered with a third data set. For example, the first data set can have been gained from a base image such as an anatomical image taken pre-operatively. The second data set can for example correspond to detector data of a first instance in time, and a third data set to detector data of a later instance in time. If the registration between the first data set, derived from the base image, and the second data set has been successful, the similarity between the second and third data set, consisting of detector data, simplifies a registration if indirect registration is used as described above.

In further embodiments, a method for image generation by means of an image generating apparatus is provided. The method includes detecting radiation by means of a detector of the image generating apparatus. Detecting can take place during a detection period. The radiation can be nuclear radiation. The detector can be movable. The detector can be freely movable. The detector can be handheld. The method further includes collecting detector data for image generation by means of the evaluation system of the image generating apparatus. Typically, the detector data include information about the detected radiation. Typically, the detector data also include information about the position and/or orientation of the detector. The method further includes registering the detector data with compatible data by means of the evaluation system. In further embodiments, the compatible data are detector data. According to further embodiments, the method for image generation includes generating simulation detector data based on a base image by means of the evaluation system. The compatible data can be simulation detector data. In further embodiments, at least one comparison function is used for registering the detector data.

In further embodiments, the method includes an indirect registration of simulation detector data with detector data by means of second compatible data. In some embodiments, the second compatible data are detector data. In other embodiments, the second compatible data are second simulation detector data based on a second base image.

Comparison functions can for example be cross correlation, trans-information, block entropies, cross correlation rates, cosine measure, extended Jaccard similarity, ratio image uniformity, sums of squared distances or sums of absolute values of distances, or further comparison functions.

In further embodiments, the base image is an anatomical or body-functional image. In other embodiments, the second base image is an anatomical or body-functional image. Anatomical images can for example be a computer tomography, a magnetic resonance tomography, an ultrasonic image, an optical image, or an x-ray image. Body-functional images can for example be a positron emission tomography, short PET, a single photon emission computer tomography, short SPECT, or an optical tomography.

In further embodiments, an image generating apparatus for image generation is provided. The image generating apparatus includes a detector for detecting radiation. The detector can be movable. The detector can be freely movable. The detector can be handheld. The radiation can be nuclear radiation. The detector can be a detector for detecting during a detection period. The image generating apparatus further includes an evaluation system. The evaluation system includes an interface system for transmitting detector data for image generation to the evaluation system. Typically, the detector data include information about the detected radiation. Typically, the detector data also include information about the position and/or orientation of the detector. The interface system can be an interface system for continuously transmitting detector data to the evaluation system. The evaluation system further includes a program memory portion with a program for registering detector data with compatible data.

In further embodiments, the compatible data are detector data. According to further embodiments, the evaluation system further includes a program memory portion with a program for generating simulation detector data based on a base image. In further embodiments, the compatible data are simulation detector data. According to further embodiments, the program for registering is programmed to register detector data with compatible data by means of at least one comparison function.

According to further embodiments, the evaluation system further includes a program memory portion with a program for indirectly registering the simulation detector data with detector data by means of second compatible data. The second compatible data can be detector data. The second compatible data can be second simulation detector data based on a second base image.

The comparison function can for example be comparison functions as described above or other comparison functions. Further, the base image or the second base image can have the same or similar properties as the ones described above.

Embodiments of the invention also include registering images. These images can for example be generated from detector data or from other data sets. A registration of images can, for example, take place by maximizing the similarity or minimizing the dissimilarity of both images. For the minimization of the dissimilarity or maximization of the similarity, comparison functions can be used such as cross correlations, trans-information, block entropies, cross correlation rates, cosine measure, extended Jaccard similarity, ratio image uniformity, sums of squared distances or sums of absolute values of distances. Other information theoretic comparison functions may also be used. For the minimization or maximization process itself, optimization algorithms can be used with algorithms as the ones mentioned above or others. Images can also be registered point-wise. To this end, specifically chosen points in both images are set into relation. The selection can take place automatically or interactively. Algorithms for point-wise registration can for example be the Umeyama or the Walker algorithm.

Finally, also an indirect image registration is possible. In this case, the process includes registering a third image with a second image, registering a first image with a third image, and registering the first image with the second image using the registration of the first image with the third image. The images can be for example anatomical or body-functional images as in the case of the registration of data sets. Such images can be gained from detector data. The image can also be gained from other detectors of the detection system such as for example by means of computer tomography, magnetic resonance tomography, ultrasonic sonography, picture taking of an optical camera or of an x-ray device. Examples for organ-functional images are images gained from the detector data but also positron emission tomography, short PET, single photon emission computer tomography, short SPECT, or optical tomography.

According to further embodiments, a method for image generation includes generating a first image on the basis of a collected detector data by means of the evaluation system. In further embodiments, the method further includes a registration of the first image with the second image. For registering the first image with the second image, a minimization of the dissimilarity or a maximization of the similarity can be used. In some embodiments, a comparison function is used for the minimization or maximization. Comparison functions can be the ones listed above or other comparison functions.

According to further embodiments, a method for image generation includes registering a third image with a second image, registering the first image with a third image, registering the first image with the second image by means of registering the first image with a third image.

In some embodiments, the second image is an anatomical image. In other embodiments, the second image is a body-functional image. An anatomical image can be one of the anatomical images described above or be a different anatomical image. A body-functional image can be a body-functional image as described above or be a different body-functional image.

Quality Control

To provide high quality, in particular up-to-date high quality images, embodiments of the invention provide methods and devices for quality control of the detector data as well as of the generated images. In some embodiments quality control takes place continuously. In this way, the quality and validity of a generated image is checked. In further embodiments, the quality control takes place already during the detection period.

Figure 12:
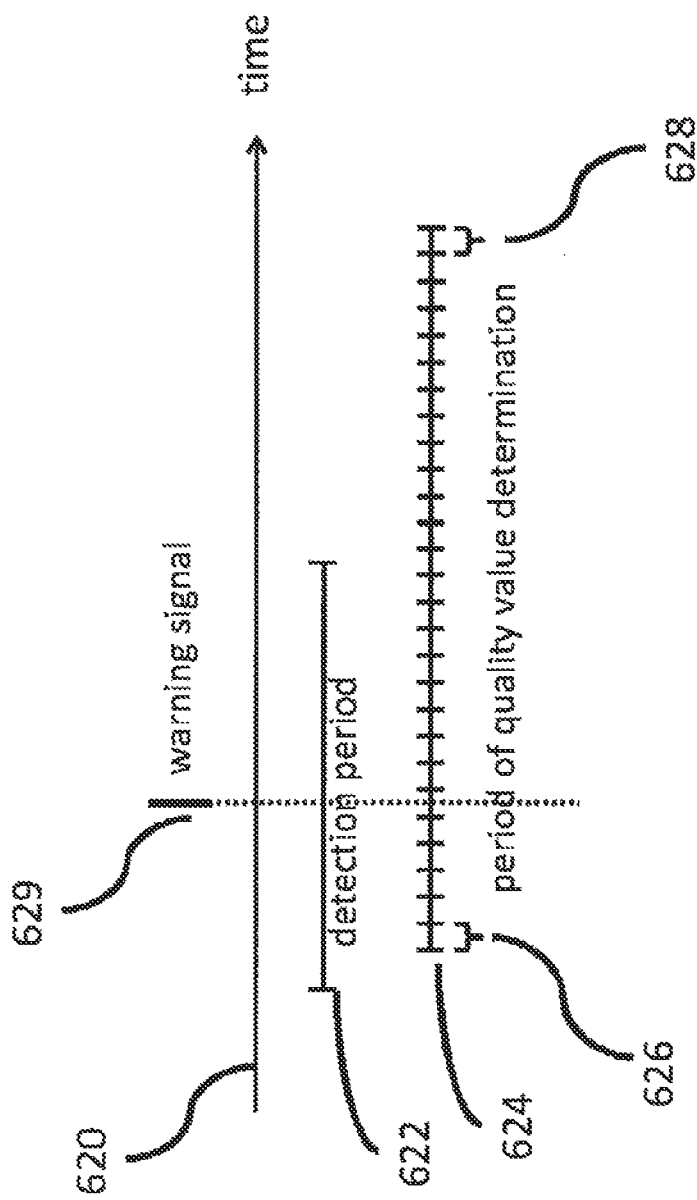
FIG. 12 shows a quality control process according to embodiments of the invention.

FIG. 12 shows a typical process of quality control according to embodiments of the invention. A time axis 620 is shown, symbolizing the course of time (from left to right). In FIG. 12, a detection period 622 is further shown. Further, with respect to the same time axis, a quality determination period 624 is depicted. Typically, the quality determination period 624 starts after the start of the detection period when detector data are already available. The quality determination period 624 can end before the detection period, at the same time as the detection period or after the detection period. Typically, the quality determination period 624 ends after the detection period. The distances between marks on the line symbolizing the quality determination period 624 symbolize themselves periods in which a quality determination process takes place, such as for example determination of a quality value by the evaluation unit. The distances 626 and 628 symbolize the first, respectively the last, quality determination process. In further embodiments of the invention, an alert signal 629 is output if data gathered, respectively collected, by the evaluation unit do not pass quality control. Such a warning signal can be output for example acoustically, optically, haptically or by combinations thereof Such a warning signal can make a user, for example a surgeon, be aware that the images determined from the detector data may not be reliable at least at the instance of time of the output of the warning signal.

Quality control is typically carried out on the basis of at least one quality criterion. With respect to one or more quality criteria, a quality value is calculated. Also, several quality values can be calculated for one, respectively more, quality criteria, for example if a quality value is determined that depends on a respective imaging region. Therein, for example, the validity or quality of an image can be rejected if such a quality value does not fulfil one ore more quality criteria, i.e. does not satisfy them. Conversely, an image can be regarded as valid if a quality value satisfies a quality criterion or satisfies several quality criteria. Here and in the following, an image can also be understood as a specified imaging region associated to the respective quality value.

Examples for a quality criteria are the following: the similarity between a first and a second image, wherein one of the images or both of the images may be generated from detector data; the conditioning of an image generation rule for generating an image; the relevance of data, such as detector data, for an image element; the plausibility of the image generation from data, such as detector data or data from a second image; the uniformity of data, such as detector data; or the risk of false generation because of faulty data, such as detector data.

The similarity between a first and a second image can be determined similarly as in the case of registration. In particular, already registered images can again be compared with each other for similarity. The images can therein have been registered by direct image registration or by data registration. The images can for example be anatomical or organ-functional images as the ones described above, or others.

If the image generation rule is, according to some embodiments, a linear rule the conditioning of the image generation rule can be given by the conditioning of the imaging matrix or the system matrix. In particular, in a linear, discrete case, the conditioning number of the imaging matrix H (see above) can be calculated. A conditioning number can be calculated by analysis of the spectrum of the singular values of the matrix or by similar matrix decomposition measures (for example relation of largest to smallest eigenvalue or number of eigenvalues being above or below a threshold value). In this example, the quality criterion is a threshold value for the conditioning number. If the calculated conditioning number, i.e. a quality value, is smaller (respectively larger, depending on the definition of the conditioning number) then the threshold value, the data, such as detector data, do not fulfil the quality criterion, and therefore an image generated therefrom is rejected. If, on the other hand, the calculated conditioning number is larger (respectively smaller) then the threshold value, the quality of the data, such as detector data, and an image reconstructed therefrom are accepted.

Similarly, the quantity named with the technical term sparsity of a matrix row or of a matrix column can be a quality value, and a threshold value with respect to this quantity can be used as a quality criterion. A row or a column of a matrix is sparse if less than a number of entries determined by the threshold value are different from zero (respectively from numerical zero, i.e., smaller than a given epsilon-threshold). If a matrix column is too sparse an image element depends on two few measurements, and therefore a high risk of false generation exists for this image element. If a matrix row is too sparse the measurement value associated with this row is responsible for two few image elements, which again may lead to a high risk or false generation.

Correspondingly, also the relevance of data for an image element can be used as a quality criterion. For a linear image generation rule the relevance of a row or column can for example be associated with a threshold value for the sum of all entries of the row or column.

The plausibility of an image generation for example takes into account a constraint. Examples for constraints are the maximal amount of radiation, the gradient of the sum of maximal radiation, minimal radiation, radiation associated to image elements that obviously cannot contain radiation sources (for example regions filled with air), and others. Depending on the degree of plausibility, a corresponding quality value can be associated.

The uniformity of detector data is determined by the spatial distribution of measurements. Uniform measurements are present if the measurements are distributed uniformly around the region to be reconstructed. A measure for uniformity is formed by the deviation of the actual measurements from a completely uniform measurement. A quality criterion is formed by a threshold value with respect to this uniformity.

In typical embodiments of the invention, a quality control based on the quality criteria named above, or on others, is carried out successively, preferably quasi-continuously (as shown in FIG. 12). In further embodiments the results of quality control is output to a user by the output system. In particular, as described above, the output can be visual, acoustical or haptic. For example, the output can take place by a coarsening of the image resolution in the corresponding image region. Thereby, a user is prevented from putting false confidence into possibly faulty images. According to further embodiments of the present invention, a method for image generation by means of an image generating apparatus is provided. The method includes detecting radiation by means of a detector. Detecting can take place during a detection period. The radiation can be nuclear radiation. The detector can be movable. The detector can be freely movable. The detector can be portable in the hand. The method further includes collecting detector data for image generation by means of an evaluation system of the image generating apparatus. In typical embodiments the detector data include information about the detected radiation. In further typical embodiments, the detector data comprise information about the position and/or orientation of the detector. The method further includes determining at least one quality value from the collected detector data by means of the evaluation system. In typical embodiments the determination is a repeated determination or a continuous determination, typically during the detection period.

In further embodiments, the method includes again, repeatedly, or continuously collecting detector data for image generation by means of the evaluation system of the image generating apparatus, preferably during the detection period.

In further embodiments, the at least one quality value is determined with respect to at least one quality criterion. A quality criterion can for example be the similarity between a first image generated from the collected detector data and a second image, the conditioning of an image generation rule for image generation from the collected detector data, the relevance of the collected detector data for an image element, the plausibility of image generation from the collected detector data, the uniformity of the collected detector data, or the risk of false generation because of faulty detector data. Apart from these, further quality criteria may be used.

Further embodiments, the method includes outputting the at least one determined quality value to a user. Further, other embodiments include outputting a warning to a user if the at least one quality value does not fulfil at least one quality criterion. Outputting the quality value or the warning can take place visually, acoustically, haptically, or by combinations thereof In further embodiments, an image generating apparatus for image generation is provided. The image generating apparatus includes a detector for a detection of radiation. The detector can be a detector for detecting radiation during a detection period. The detector can be movable. The detector can be freely movable. The detector can be variable in the hand. The detector can be nuclear radiation. The image generating apparatus further includes an evaluation system. The evaluation system includes an interface system for transmitting detector data for image generation to the evaluation system. Typically, detector data include information about the detected nuclear radiation. Typically, the detector data further include information about the position and/or orientation of the detector. The evaluation system further includes a data memory portion for storing the detector data. The evaluation system further includes a program memory portion with a program for determining at least one quality value with respect to image generation from the detector data. The program can also be a program for again, repeatedly, or continuously determining at least one quality value with respect to image generation from the detector data. Therein, determining at least one quality value can take place during a detection period.

In further embodiments, the interface system is an interface system for again, repeatedly, or continuously transmitting detector data to the evaluation system. The transmission can take place during the detection period. The detector data can include information about the detected radiation. The detector data can also include information about the position and/or orientation of the detector.

In further embodiments, the program for determining at least one quality value is a program for determining, again determining, repeatedly determining, or continuously determining a quality value with respect to at least one quality criterion.

In further embodiments, the image generating apparatus for image generation further includes an output system, which includes at least one output unit. In further embodiments, the output unit is an output unit for outputting the at least one determined quality value to a user. In further embodiments, the output unit or a further output unit is an output unit for outputting a warning to a user if the at least one quality value does not fulfil at least one quality criterion. The one output unit or the other output unit can be output units for instructions or warnings to the user in visual, acoustical, or haptical form, or in combination forms thereof The outputs can be combined with an instruction to a user for improving the quality value, as described further below.

Enhancement of Image Generation

According to embodiments of the invention, methods and apparatuses for image generation are provided in which the quality of image generation is enhanced. In typical embodiments, a quality is continuously enhanced. In particular, the quality can already be enhanced, or continuously enhanced, during the detection period.

In typical embodiments, the image generation takes place on the basis of a linear image generation rule. This image generation can for example take place by applying an imaging matrix or system matrix H to a vector f wherein H and f have denotations explained above. The image generation can, as described above, take place by comparison of the result vector $g=H*f$ with the detector data vector $g_{measured}$ (respectively by equivalent methods). The image generation, also called reconstruction, takes place by minimization of the distance between the vector g and the vector $g_{measured}$ as a function off as described above.

An improvement of image generation can take place by different ways that include: improving the starting value of vector f in the minimization problem, enhancing the image generation rule, in particular the image matrix H.

As starting value for the minimization problem, a vector $f_{start}$ can for example be used, the contained information of which is derived from a given image, for example from a pre-operative anatomical or organ-functional image. This helps to avoid getting a wrong solution while solving the minimization problem (such as being trapped in a local minimum that does not correspond to the desired solution). Also, the computing time can be decreased because one starts with a nearly correct solution already. In this way, a good solution of the minimization problem, i.e. a good image f, can be obtained with reduced effort.

An improvement of the imaging rule, respectively of the imaging matrix H, can in particular take place by calculating at least one quality value, wherein the quality value is the same as in the quality control of data described above, or can be a further quality value. Additionally, the imaging matrix H is modified while taking into account a quality value. In particular, the imaging matrix H is modified in such a way that the modified matrix H better satisfies one or several quality criteria.

For example, rows or columns can be eliminated which have been recognized as being too sparsely filled according to a threshold with respect to the sparsity of a matrix. Likewise, rows or columns of the imaging matrix H can be eliminated which do not satisfy the criterion of relevance. Instead of pure elimination, such rows or columns can be combined, whereby also the corresponding image elements (entries of f), respectively detector measurement values (entries of g), are correspondingly combined.

The uniformity can further be improved, for example by combining the detector data of neighbouring measurements such that rather uniformly distributed effective measurements are obtained. By such combinations, the imaging matrix becomes smaller, and also for this reason the reconstruction is numerically better solvable.

On the other hand, information may be lost by such combination. To compensate the loss of information at least partially, a higher weight can be attributed to the entries averaged from several values, which takes into account their higher statistical significance. For example, the contribution of such entries to the distance norm |•| can receive a higher weight.

According to further embodiments, the following further methods are used for enhancing image generation:

Use of Surface Information

If the surface of the spatial region containing the radiation source is known, possible mappings can be eliminated that contain information about image elements which do not lie within this surface. In particular, this surface can for example be the surface of the body of a patient. This surface can be scanned by a laser range scanner, a laser surface pattern scanner, a laser pointer surface scanner, stereoscopic camera systems, time-of-flight cameras and further surface capturing systems.

Such surface information can also be determined on the basis of the geometry of an object tracked by the tracking system and its tracked trajectory: if an object cannot penetrate into the patients tissue, then the spatial areas traversed by this objet must be filled with air and can hence not contain any radiation sources. In particular, this object can be formed by the detector itself or be integral with the detector.

Use of Anatomical Information

If, for example in the case of medical imaging, the anatomy in a region of the generated image is known, constraints can be set on the basis of the knowledge of the anatomy and can be taken into account. A constraint can for example be that body part such as bones or the air tube (which, for example with a certain tracer, cannot form nuclear radiation sources) cannot show any radiation activity. In this way, possible mappings can be eliminated that would falsely ascribe a radiation activity to such regions. Anatomical information can for example be obtained by anatomic images captured before. These can be registered with current data. Also, standard data can be used, for example from anatomic atlases, which can also be registered with currently generated images. Anatomical information can also be presently obtained by further detectors of the detection system, such as for example ultrasonic devices, computer tomographs, radiographs, optical cameras, magnetic resonance tomography devices, and others.

Use of Further Radiation Detectors

The detection system can include further radiation detectors. Further detector data can also be used for image generation. Turther detectors can be radiation detectors, in particular radiation detectors for nuclear radiation. The further detectors can be movable radiation detectors. The further radiation detectors can also be fixed radiation detectors. For instance, the table on which the radiation distribution lies may include a gamma camera. In further embodiments, floor, sealing, and/or wall-mounted detectors are used.

According to further embodiments, a method for image generation by means of an image generating apparatus is provided. The method includes detecting radiation by means of the detector of the image generating apparatus. Detecting can take place during a detection period. The radiation can be nuclear radiation. The detector can be movable. The detector can be freely movable. The detector can be handheld. The method further includes collecting detector data for image generation by means of an evaluation system of the image generating apparatus. Typically, the detector data include information about the detected radiation. Typically, detector data also include information about the position and/or orientation of the detector. The method further includes determining an image generation rule by means of the evaluation system on the basis of the collected detector data. The method further includes modifying the image generation rule on the basis of at least one quality value. In typical embodiments, the modification is a repeated or continuous modification of the image generation rule. Typically, modifying takes place during the detection period.

In further embodiments, the collection of detector data is an anew, repeated, or continuous collection of detector data. In further embodiments, the determination of an image generation rule is an anew, repeated, or continuous determination of an image generation rule. Typically, determining, again determining, repeatedly determining, or continuously determining takes place during a detection period.

In further embodiments, the at least one quality value is determined with respect to at least one quality criterion. Quality criteria can be the same as the ones described in the section about the quality control, or can be further quality criteria. Further quality criteria can be criteria on the basis of constraints. Such constraints can consist of using surface information, anatomical information or other information. Also, use of further radiation detectors can be made, and thus further detector data for modifying, again modifying, repeatedly modifying or continuously modifying the image generation rule can be used.

In further embodiments, an image generating apparatus for image generation is provided. The image generating apparatus includes a detector for detecting radiation. The detector can be a detector for detecting during a detection period. The detector can be movable. The detector can be freely movable. The detector can be handheld. The radiation can be nuclear radiation. The image generating apparatus further includes an evaluation system. The evaluation system includes an interface system for transmitting detector data to the evaluation system for image generation. Detector data typically also include information about the position and/or orientation of the detector. The evaluation system further includes a data memory portion for storing detector data. The evaluation system further includes a program memory portion with a program for determining an image generation rule on the basis of the collected detector data. The evaluation system further includes a program memory portion with a program for modifying the image generation rule on the basis of at least one quality value. The modification is typically an anew, repeated, or continuous modification of the image generation rule. The program for modifying, again modifying, repeatedly modifying or continuously modifying the image generation rule is, according to typical embodiments, a program for modifying, again modifying, repeatedly modifying, or continuously modifying the image generation rule on the basis of at least one quality value during the detection period.

In further embodiments, the interface system is an interface system for again, repeatedly, or continuously transmitting detector data to the evaluation system. Typically the transmission is a transmission during a detection period.

In typical embodiments, the program for determining at least one quality value is a program for determining at least one quality value with respect to at least one quality criterion. Quality criteria can be the ones described above in the section "quality control", or can be other quality criteria.

In further embodiments, the image generating apparatus further includes an output system with at least one output unit. In further embodiments, the output unit is an output unit for outputting the at least one determined quality value to a user. In other embodiments, the output unit is an output unit for outputting a warning to a user if the at least one quality value does not satisfy at least one quality criterion. Outputting a quality value or a warning to a user can take place in visual, acoustical, or haptic form, or in a combination form thereof.

Outputting an Instruction to a User

Embodiments of the present invention include outputting an instruction to a user. A user can be a human user. A user can also be another living being. Alternatively, a user can also be an inanimate object, for example a machine. In particular, typical embodiments include outputting of an instruction to a user for further moving the detector in dependence on the detector data already collected. Typical embodiments include a continuous instruction for detection on the basis of a continuous quality control, which has been described above. The output takes place by means of the output system, in particular in optical, acoustical or haptic form, or by combinations thereof. Specifically, instructions for further movement of the detector are given in such a way that, when followed, a quality of the collected detector data is improved. Typically, instruction for further moving the detector in dependence of the collected data is output such that, if followed, the quality of the detector data is presumably enhanced the most. Instructions can for example take place in form of outputting an arrow pointing in the direction in which further measurements shall be made.

Typically, the calculation of the current quality or rating or validity of the collected detector data precedes the outputting of an instruction, and also a calculation how the quality of the data would change if further detector data were available, in particular detector data with information about the detected radiation measured from different orientations or positions of the detector.

Figure 13:
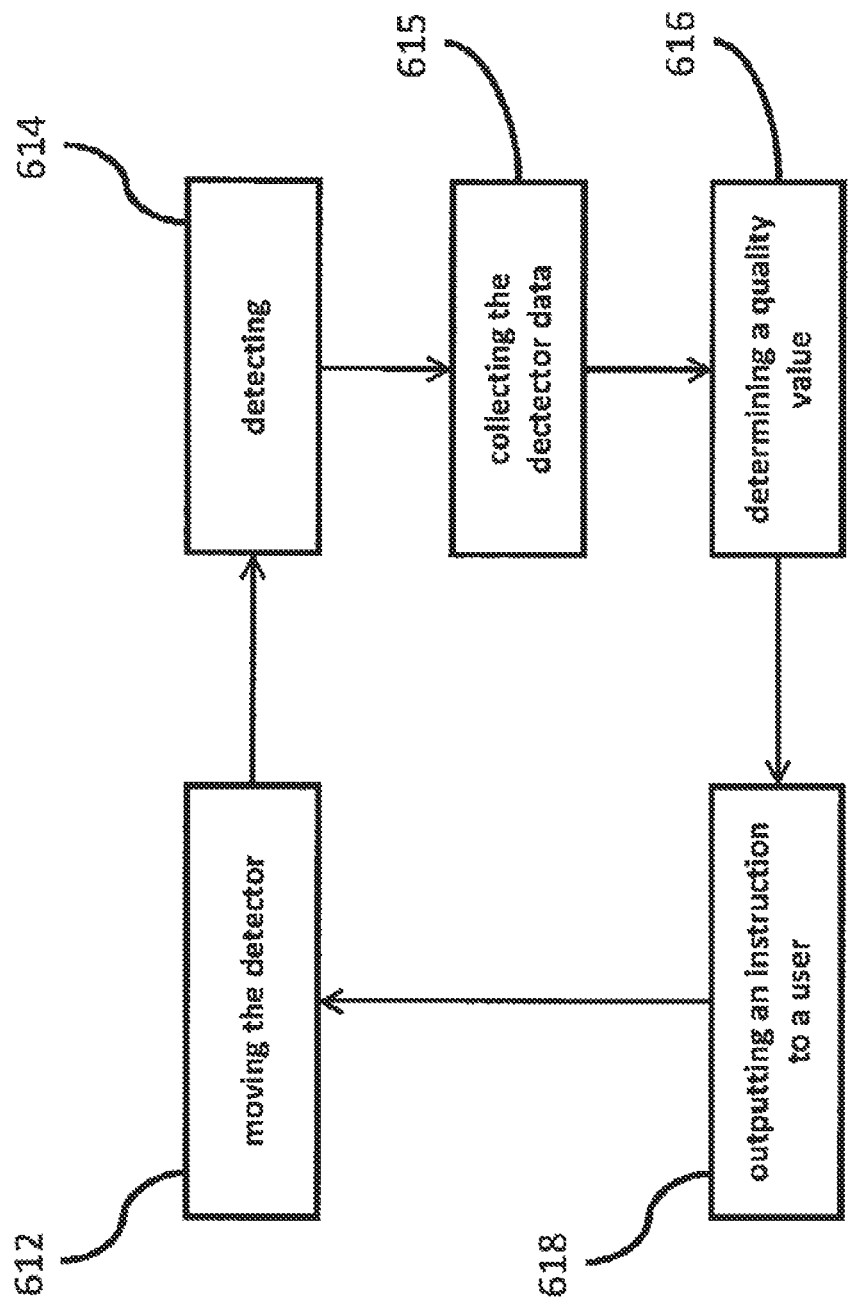
FIG. 13 shows an iterative flow diagram with a step of instructing a user according to embodiments of the invention.

FIG. 13 shows iterative method steps according to embodiments of the invention. One of the iterative steps is a movement of the detector. In typical embodiments, a freely movable, for example carryable detector is used. After or during movement, detection 614 of radiation by the detector takes place. Afterwards, or simultaneously, a collection 615 of detector data with information about the detected radiation is carried out by the evaluation system. Typically, further detector data such as position and/or orientation of the detector collected, normally synchronized with the detector data with information about the detected radiation. On the basis of the detector data, a determination 616 of a quality criterion takes place by the evaluation unit. Then, an output 618 of an instruction to a user takes place. According to embodiments of the invention, the output 618 instructs a user to move the detector in a way that a movement corresponding to the instruction leads to the subsequent measurement of suitable detector data. Suitable detector data are typically detector data that enhance image generation.

Typically, such a position and/or orientation of the detector is output to the user that would presumably enhance the quality the most. An output, for example in acoustical form, can be represented in form of an intensifying signal sound. An output in haptic form can, for example, be the provision of a sensation of resistance or of being pulled. This sensation can for example be effected by mechanical guidance or by electrical stimulation of muscles or of the brain.

To compute the orientations and positions which presumably enhance imaging, anatomical or organ-functional images can also be used.

According to further embodiments, a method for image generation by means of an image generating apparatus is provided. The method includes detecting radiation by means of a detector of the image generating apparatus. Detection can take place during a detection period. The radiation can be nuclear radiation. The detector can be movable. The detector can be freely movable. The detector can be handheld. The method further includes collecting detector data for image generation by means of an evaluation system of the image generating apparatus. Typically, detector data include information about the detected radiation. Typically, the detector data also include information about the position and/or orientation of the detector. The method further includes outputting an instruction to a user for further moving the detector in dependence of the collected detector data. According to typical embodiments, the instruction relates to at least a part of the remaining detection period.

According to further embodiments, the collection is an anew, repeated, or continuous collection of detector data. In further embodiments, outputting an instruction is again, repeatedly, or continuously outputting an instruction to a user for further moving the radiation detector. In typical embodiments, the outputting, anew outputting, repeated outputting or continuous outputting of an instruction to a user for further moving the radiation detector includes outputting the position and/or orientation of the detector that, if adopted by the detector, would enhance image generation according to at least one quality value in a accordance with a prediction. Typically, the positions and/or orientations are output, which, if assumed by the detector, would most enhance image generation according to a quality value in light of a prediction. Outputting can take place visually, acoustically, haptically, or by combinations thereof In further embodiments, an image generating apparatus for image generation is provided. The image generating apparatus includes a detector for detecting radiation. The detector can be a detector for detecting radiation during a detection period. The detector can be movable, freely movable, or handheld. The radiation can be nuclear radiation. The image generating apparatus further includes an evaluation system. The evaluation system includes an interface system for transmitting detector data for image generation to the evaluation system. Detector data typically include information about the detected radiation. Detector data typically also include information about the position and/or orientation of the detector. The evaluation system further includes a data memory portion for storing the detector data. The image generating apparatus further includes an output system for outputting an instruction to a user how to further move the detector in dependence of the detector data. In typical embodiments, the instruction relates to at least a part of the remaining detection period.

In further embodiments, the interface system is an interface system for again, repeatedly, or continuously transmitting detector data to the evaluation system. In further embodiments, the output system for outputting an instruction to a user is an output system for outputting an anew, repeated, or continuous instruction to a user for further moving the detector in dependence of the detector data. Typically, the instructions relate to at least a part of the remaining detection period. In typical embodiments, the output unit is an output unit for outputting the position and/or orientation of the detector which, if assumed by the detector, would enhance, and preferably most enhance, image generation according to at least one quality value in accordance with a prediction. The output unit can be an output unit for an output in visual, acoustical, or haptic form or in a combination form thereof.

Freehand Acquisition

Intrinsic problems of processing detector data, which occur in particular with a freely movable detector or a freehand detector, arise because measurements can take place in principle at each instant in time and with arbitrary position and/or orientation of the detector. Thereby, data may be gathered while the detector is not pointed towards the radiation source that is to be detected. Similarly, further sources for unsuitable data exist. Such data can deteriorate image generation. Such unsuitable data can deteriorate an imaging matrix, for example with respect to relevance or sparsity.

Figure 14:
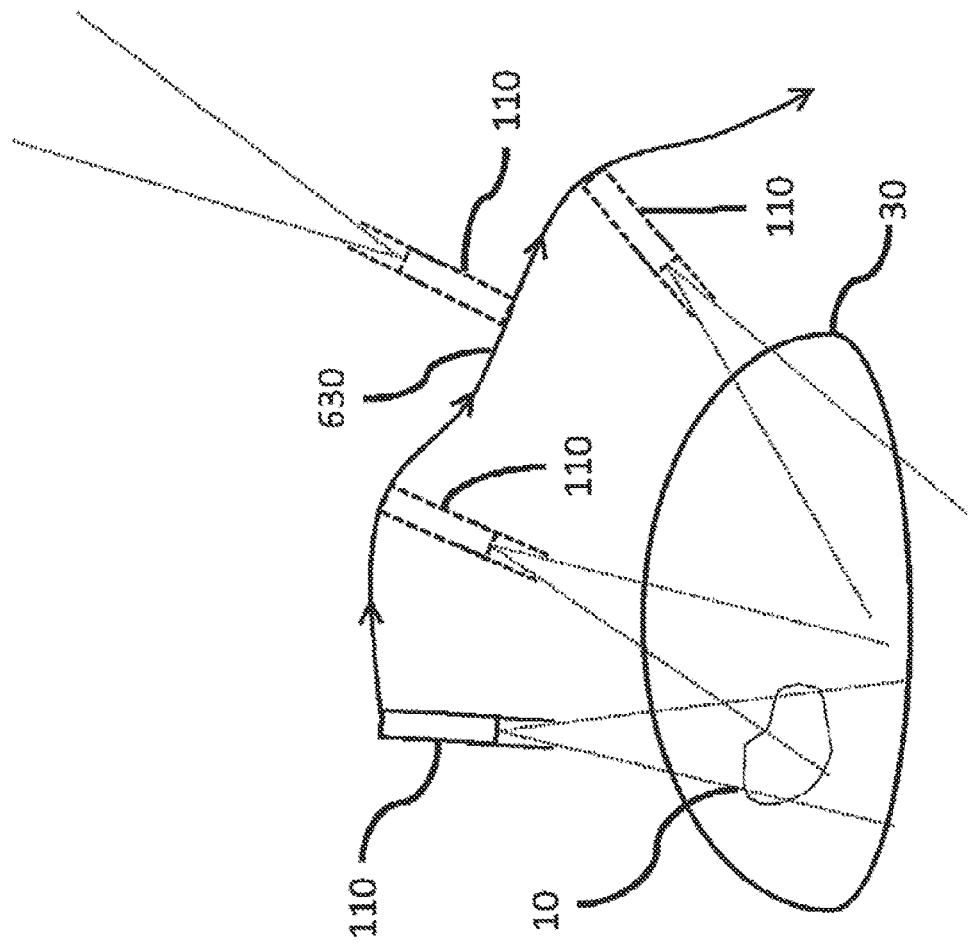
FIG. 14 shows a detection process with a freely movable detector according to embodiments of the invention.

FIG. 14 shows a freely movable detector 110 being moved along an arbitrary trajectory. The movement direction is indicated by arrows along the trajectory. Positions and orientations that follow in time to a first position and orientation are depicted with dashed lines. The detector 110 measures the emissions of a radiation source 10 within a spatial region 30 at different, generally arbitrary instances in time. The radiation source 10 can for example be a nuclear radiation distribution in the body of a living being. FIG. 14 shows at least one position and orientation 630 of the detector which presumably leads to unsuitable detector data with respect to the measured radiation. Unsuitable detector data typically deteriorate image generation.

For this and other reasons, data acquisition with freely movable detectors needs quality control even more than detection with fixed or limitedly movable detectors. Besides quality control, an improvement of the image generation rule can take place.

According to embodiments of the invention, a quality control and/or an active enhancement of the image generation rule takes place during the detection period, in contrast to a post selection. In typical embodiments, quality control takes place repeatedly or successively, typically quasi-continuously or continuously.

Likewise, the enhancement of an imaging rule can take place repeatedly or successively, typically quasi-continuously or continuously. An enhancement can take place as for example described in the section "enhancing image generation" or in another way.

According to further embodiments, a method for image generation by means of an image generating apparatus is provided. The method includes detecting radiation by means of a movable detector of the image generating apparatus. Typically, detecting takes place during a detection period. The detector can be freely movable. The detector can be handheld. The radiation can be nuclear radiation. The method further includes changing the position and/or orientation of the detector. In typical embodiments, changing the position and/or orientation of the detector takes place during the detection period. Changing can be freely changing the position and/or orientation of the detector. Changing can also be again, repeatedly, or continuously changing. The method further includes collecting detector data for image generation by means of the evaluation system of the image generating apparatus. Typically, collecting is again, repeatedly, or continuously collecting detector data. Typically, collecting takes place during the detection period. The detector data usually include information about the detected radiation. The detector data usually also include information about the position and/or orientation of the detector. The method further includes determining at least one quality value from the collected detector data by means of the evaluation system.

In further embodiments, determining at least one quality value takes place again, repeatedly, or continuously, typically during the detection period. In further embodiments, the at least one quality value is determined with respect to at least one quality criterion. Quality criteria can for example be the quality criteria described in the section "quality control", or can be other quality criteria.

According to further embodiments, an image generating apparatus for image generation is provided. The image generating apparatus includes a movable detector for detecting radiation. The movable detector is, according to typical embodiments, a detector for detecting radiation during a detection period. The detector can be freely movable. The detector can be handheld. The radiation can be nuclear radiation. The image generating apparatus further includes an evaluation system. The evaluation system includes an interface system for continuously transmitting detector data for image generation to the evaluation system. Typically, detector data include information about the detected radiation. Typically, detector data include also information about the position and/or orientation of the detector. According to further embodiments, the interface system is an interface system for continuously transmitting the detector data during the detection period. The evaluation system further includes a data memory for storing the detector data. The evaluation system further includes a program memory portion with a program for determining at least one quality value with respect to image generation from the detector data. According to further embodiments, the program for determining at least one quality value is a program for again, repeatedly, or continuously determining at least one quality value with respect to image generation from the detector data. In typical embodiments, the program for determining at least one quality value is a program for determining, again determining, repeatedly determining, or continuously determining at least one quality value with respect to image generation from the detector data during the detection period.

In further embodiments, the program for determining at least one quality value is a program for determining at least one quality value with respect to at least one quality criterion. The at least one quality criterion can be a quality criterion as described in the section "quality control", or can be a further quality criterion.

According to further embodiments of the invention, which can be combined with any of the embodiments, the method for image generation includes generating an image by minimization of the dissimilarity or maximization of the similarity, wherein preferably at least one reconstruction method for minimization or maximization is used. The at least one reconstruction method can be an algebraic reconstruction method, short ART, a maximum likelihood expectation value maximization algorithm, short MLEM, an iterative matrix inversion method such as the Jacobi method, the Gauss-Seidel method, or the over-relaxation method, a direct matrix inversion method such as the singular value decomposition or a regularised matrix inversion method such as the singular value decomposition with Tikhonov regularization.

According to further embodiments of the invention, which can be combined with other embodiments, the method for image generation is a method for image generation for medical purposes. According to further embodiments, the method for image generation includes collecting body data of a living being by means of the evaluation system. Typically, body data include respiration frequency and/or heartbeat frequency. Typically, the body data also include data with respect to form, position and/or orientation of the body. In further typical embodiments, the body data with respect to respiration frequency and/or heartbeat frequency are synchronized with the body data with respect to form, position and/or orientation of the body, and are collected in synchronized way. The gathering of body data of the living being can for example be effected by the tracking system.

According to further embodiments, the method for image generation further includes modifying the image generation rule on the basis of the collected body data. Thereby, movements of the body, for example by respiration or heartbeat, can be taken into account for image generation. This leads to an enhanced image generation. Also, registration of images or the registration of detector data is facilitated thereby.

According to further embodiments, that can be combined with other embodiments, the method for image generation includes gathering of data of at least one instrument, preferably a medical instrument, by means of the evaluation system. According to further embodiments, the method further includes a registration of data of medical instruments with respect to data and/or simulation detector data by means of the evaluation system. In typical embodiments, the method further includes generation of a combination image on the basis of the registration.

According to further embodiments, the method further includes a tracking of data of medical instruments by the tracking system.

According to further embodiments, the method includes generating an instrument image on the basis of the collected instrument data by means of the evaluation system. According to further embodiments, the method further includes a registration of the instrument image with the first image and/or the second image and/or the third image and/or with an already registered image. Further, the method typically includes generating a combination image on the basis of the registration.

According to further embodiments, the method includes outputting a combination image by means of the output system. According to further embodiments, the method includes instructing a user, on the basis of the combination image, how to use the medical instruments. According to yet further embodiments, the method includes guiding a user while using the medical instruments by means of a guiding system on the basis of the instrument data. The guiding system can include a guiding unit guiding a user in haptic, acoustic or visual way, or by combinations thereof.

In particular, instructing the user, on the basis of a combination image, on how to use the medical instruments, or guiding the user while using the medical instruments by a guiding system can take place for example by visualization of a virtual reality, visualization of an augmented reality, by layer and multi-layer visualization, frequency-modulated sound, amplitude-modulated sound, pulse-modulated sound, by combinations thereof, or in any other way.

According to further embodiments, the method for image generation includes positioning the living being. Positioning can take place for example by a positioning system which includes a positioning unit. Such a positioning unit can position the living being in any desired position and/or orientation according to some embodiments.

According to further embodiments of the invention, the image generating apparatus for image generation is an image generating apparatus for image generation for medical purposes. According to further embodiments, the image generating apparatus includes at least one sensor for detecting body data of a living being. Typically, the body data include respiration frequency and/or heartbeat frequency of the living being. According to further embodiments, the image generating apparatus includes a tracking unit for gathering body data of the living being. Typically, the body data include the form, position and/or orientation of the body. According to further embodiments, the evaluation system further includes a program memory portion with a program for synchronized collection of body data of the living being. Typically, the evaluation system further includes a data memory portion for storing the synchronized body data of the living being. According to further embodiments, the evaluation system further includes a program portion with a program for modifying the image generation rule on the basis of the collected body data.

According to further embodiments, the evaluation system of the image generating apparatus further includes an interface for collecting data of at least one instrument, typically of at least one medical instrument. Further, the evaluation system includes, according to embodiments of the invention, a program memory portion with a program for generating an instrument image on the basis of the instrument data.

According to further embodiments, the evaluation system includes a program memory portion with a program for registering data of medical instruments with detector data and/or simulation detector data. Further, the evaluation system includes a program memory portion with program for generating a combination image on the basis of the output of the program for registering the data of medical instruments according to some embodiments.

According to further embodiments, the evaluation system includes a program memory portion with a program for registering the instrument image with the first image and/or the second image and/or the third image and/or with an already registered image. Further, the evaluation system typically includes a program memory portion with a program for generating a combination image on the basis of the output of the program for registering the instrument image.

According to further embodiments, the output system of the image generating apparatus includes an output unit for output of the combination image. According to further embodiments, the output system includes an output unit for instructing a user how to use the medical instruments on the basis of the combination image. According to further embodiments, the image generating apparatus includes a guiding system for guiding the user while using the medical instruments on the basis of the instrument data. The guiding system includes at least one guiding unit.

The output unit for instructing a user how to use the medical instruments on the basis of the combination image as well as the guiding system for guiding the user while using the medical instruments can communicate signals to the user in haptic, acoustic, or visual form, or in a combination form thereof The output unit can also be identical with the guiding unit of the guiding system. The output unit can also be different from the guiding unit of the guiding system. The output unit and/or the guiding unit can be units for visualization of a virtual reality, for visualization of an augmented reality, for layer and multilayer visualization, for frequency-modulated sound output, for amplitude-modulated sound output, for pulse-modulated sound output, or for output of combinations thereof, or can be units for output in a different way.

According to further embodiments of the invention, the image generating apparatus further includes a positioning system for positioning the living being. The positioning system includes at least one positioning unit. In typical embodiments, the positioning unit can position the living being in any desired position and/or orientation in space.

In the following some additional embodiments will be described (embodiments 1 to 30):

1. A device for intra-operative 3D-nuclear imaging, 3D-visualization and image-guided surgery based on pre-operative data and tracked radiation detectors, wherein the device includes: (a) a radiation detector; (b) a tracking system for synchronously tracking the position and orientation of said radiation detector and for readout; (c) a pre-operative nuclear image; (d) a data processing system which communicates with the radiation detector and with the tracking system and is adapted to read the pre-operative nuclear image for allowing a three dimensional reconstruction of the nuclear image and/or the computation of a corresponding quality value from a list of readout data, positions and orientations of the radiation device and the pre-operative nuclear image; and (e) a display for displaying the reconstructed image.

2. A device for intra-operative three dimensional nuclear imaging, 3D-visualization and image-guided surgery based on pre-operative data and tracked radiation detectors, the device including: (a) a radiation detector; (b) a tracking system for tracking the position and orientation of the radiation detector and of its readout data in synchronized form; (c) a pre-operative nuclear image; (d) a data processing system which communicates with the radiation detector and with the tracking system and is able to read the pre-operative nuclear image for allowing the spatial registration of the list of readout data, positions and orientations of the radiation device; and (e) display for displaying the registered images.

3. A device for intra-operative three dimensional nuclear imaging, three dimensional visualization and image-guided surgery, based on pre-operative data and tracked radiation detectors as described in the embodiment 2 and also including a system for correct patient positioning based on the output of the registration.

4. A device for intra-operative three dimensional nuclear imaging, three dimensional visualization and image-guided surgery, based on pre-operative data and tracked radiation detectors as described in the embodiments 1 and 2, and further including: (a) a three dimensional imaging device; (b) a second tracking system which is the same as the first tracking system or which communicates with the first tracking system and is co-registered with it and determines the position and orientation of the three dimensional imaging device; and (c) a second data processing unit, which is the same as the first data processing system or which communicates with the first data processing system, and which communicates with the three dimensional imaging device and with the second tracking system, thereby enabling to determine the position and orientation of the body part that is imaged, and thus to calculate the relative position and orientation of the body part that is imaged and the radiation detector and to allow a movement and deformation compensation; and or to allow attenuation and/or scattering correction based on the three dimensional images.

5. A device for intra-operative 3D-nuclear imaging, 3D-visualization and image-guided operation, based on pre-operative data and tracked radiation detectors as described in embodiment 4, wherein the three dimensional imaging device is of such form that it generates for example ultrasonic images, x-ray based images, magnetic resonance tomography images, optical images, contrast-enhanced ultrasonic images, contrast-enhanced x-ray-based images, functional magnetic resonance tomography images, dye-based optical images, fluorescence images, reflection images, auto-fluorescence images, etc.

6. A device for intra-operative three dimensional nuclear imaging, three dimensional visualization and image-guided surgery, based on pre-operative data and tracked radiation detectors as described in the embodiments 1 or 2, further including: (a) artificial markings which are positioned on or in the body part to be images; and (b) a second tracking system, which is the same as the first tracking system or which communicates with the first tracking system, and which determines the position and orientation of the artificial markings and communicates with the data processing unit, such that it allows to calculate the position and orientation of the body part that is imaged and of the radiation detector and allows movement and/or deformation compensation.

7. A device for intra-operative three dimensional nuclear imaging, three dimensional visualization and image-guided surgery, based on pre-operative data and tracked radiation detectors as described in the embodiments 1 or 2, and also including a calibrated sensor for monitoring the position and orientation of the body part that is imaged, wherein the sensor communicates with the data evaluation unit, such that it allows to calculate the relative position and orientation of the body part this is imaged and of the radiation detector and allows movement and/or deformation compensation.

8. A device for intra-operative 3D-nuclear imaging, three dimensional visualization and image-guided surgery, based on pre-operative data and tracked radiation detectors as described in the embodiments 1 or 2, and also including a sensor for monitoring the respiration and a heart signal of the patient, wherein the sensor communicates with the data processing unit, such that a phase label is attached to each readout, position and orientation of the radiation detector, such that movement and/or deformation compensation for respiration, heartbeat, or both is possible.

9. A device for intra-operative 3D-nuclear imaging, 3D-visualization and image-guided surgery, based on pre-operative data and tracked radiation detectors as described in any of the preceding or following embodiments, further including: (a) at least one surgical instrument and (b) a third tracking system for tracking the surgical instrument, wherein the third tracking system is the same as the first tracking system or communicates with a first tracking system, such that the relative position and orientation of the surgical instrument and of the reconstructed three dimensional image or registered pre-operative image can be calculated and can be used for (a) guiding instruments to regions of increased accumulation; (b) guiding instruments away from regions of increased accumulation; (c) guiding instruments to regions of low accumulation; (d) guiding instruments away from regions of low accumulation; (e) simulating, at the tip of each instrument, the radiation readout that each instrument would give if it were a gamma probe; (f) displaying surgical instruments on the display; and/or (g) detecting when the validity of the images is lost because of the operation in the reconstructed or registered volume by means of the instruments, and warning a surgeon.

10. A device for intra-operative 3D-nuclear imaging, 3D-visualization and image-guided surgery, based on pre-operative data and tracked radiation detectors as described in any of the preceding or following embodiments, further including: (a) a display of virtual reality and/or (b) a display of augmented reality, such that the reconstructed 3D-gamma-emitting images and the registered pre-operative images can be displayed three dimensionally in visual, acoustic, haptic or in a combined way, and/or in particular spatially registered with the image geometry of some camera, wherein the camera includes laparoscope cameras and cameras based on surgical microscopes, optical and image-transparent head-mounted displays, optical and image-transparent, stereoscopic surgical microscopes, optical and image-transparent displays.

11. A device for intra-operative 3D-nuclear imaging, 3D-visualization and image-guided surgery, based on pre-operative data and tracked radiation detectors as described in any of the preceding or any of the following embodiments, wherein the radiation detector is one of the following: gamma probe; beta probe; gamma camera; beta camera; mini gamma camera; or a combination thereof.

12. A device for intra-operative 3D-nuclear imaging, 3D-visualization and image-guided surgery, based on pre-operative data and tracked radiation detectors as described in any of the preceding or any of the following embodiments, wherein the tracking systems are external tracking systems, for example including optical tracking systems, magnetic tracking systems, mechanical or robot arm-based systems, radio wave-based tracking systems, sound wave-based tracking systems, etc., or internal tracking systems, which for example include acceleration detector-based tracking systems, potentiometer-based tracking systems, etc., or a combination of external tracking systems and/or internal tracking systems.

13. A device for intra-operative 3D-nuclear imaging, 3D-visualization and image-guided operation, based on pre-operative data and tracked radiation detectors as described in any of the preceding or any of the following embodiments, wherein the displays are the following: (a) visual displays, for example monitor systems, which for example include: monitors, optically transparent monitors, stereo monitors, stereo-optically transparent head mounted displays, etc.; (b) acoustical displays, which for example include frequency-coded feedback systems, pulse-coded feedback systems, etc.; (c) haptic displays, which for example include force feedback joysticks, force-torque feedback joysticks, etc., or (d) some combination of visual, acoustical and/or haptic displays.

14. A device for intra-operative 3D-nuclear imaging, 3D-visualization and image-guided surgery, based on pre-operative data and tracked radiation detectors as described in any of the preceding or following embodiments, further including: (a) a memory system for the involved information, which communicates with a first and second data processing unit and/or (b) a third data processing unit, which communicates with a first and second data processing unit, such that the full information or a part thereof is stored as documentation material and/or an automatic report of the procedure is generated.

15. A device for intra-operative 3D-nuclear imaging, 3D-visualization and image-guided operation, based on pre-operative data and tracked radiation detectors substantially as described herein and with reference to and/or as illustrated in the appended drawings.

16. A device for intra-operative 3D-nuclear imaging, 3D-visualization and image-guided operation, based on pre-operative data and tracked radiation detectors as described in any of the preceding or following embodiments, and further including a sensor and/or a further data processing unit, which can be the same as the first data processing unit or can communicate with a first data processing unit for the online calculation or the tracking of errors in the position and orientation of any of the tracked objects and/or errors in the readout of the radiation record.

17. A method for intra-operative, 3D-nuclear imaging, 3D-visualization and image-guided surgery, based on pre-operative data and tracked radiation detectors, including: (a) detection of radiation by means of a radiation detector; (b) synchronized tracking of the position and orientation of the radiation detector and its readings; (c) readout of at least one pre-operative nuclear image; (d) 3D-reconstruction of a nuclear image from a list of readings, positions and orientations of the radiation device and of the pre-operative nuclear image and/or the computation of a corresponding quality value; and (e) displaying the reconstructed image.

18. A method for intra-operative 3D-nuclear imaging, 3D-visualization and image-guided operation, based on pre-operative data and tracked radiation detectors, including: (a) detection of radiation by means of a radiation detector; (b) synchronized tracking of position and orientation of the radiation detector and its readings; (c) readout of at least one pre-operative nuclear image; (d) spatially registering a list of readings, positions and orientations of the radiation device; and (e) displaying the registered image.

19. A method for intra-operative 3D-nuclear imaging, 3D-visualization and image-guided operation, based on pre-operative data and tracked radiation detectors as described in the embodiment 16, wherein the registration is successful by back projection of the readout data, positions and orientations of the radiation detector on a 3D-radioactive distribution.

20. A method for intra-operative 3D-nuclear imaging, 3D-visualization and image-guided operation, based on pre-operative data and tracked radiation detectors as described in embodiment 16, wherein the registration is successful by forward projection of the pre-operative nuclear image on the positions and orientations of the radiation detector.

21. A method for intra-operative 3D-nuclear imaging, 3D-visualization and image-guided operation, based on pre-operative data and tracked radiation detectors as described in embodiment 16, further including: (a) correctly positioning a patient based on the output of the registration; and/or (b) adaptation of surgery plans, wherein the output is used.

22. A method for intra-operative 3D-nuclear imaging, 3D-visualization and image-guided surgery, based on pre-operative data and tracked radiation detectors as described in the embodiments 15 or 16, further including: (a) generation of 3D-images by using 3D-imaging devices; (b) synchronized tracking of position and orientation of the 3D-imaging devices; (c) determination of position and orientation and/or of the deformation of the body part that is imaged from the 3D-images; (d) the calculation of relative positions and orientations and deformations of the body part that is imaged and of the radiation detector; (e) the compensation of movement and/or deformation of the body part that is imaged on the basis of this relative position and orientation and/or compensation of the attenuation and/or scattering based on 3D-images.

23. A method for intra-operative 3D-nuclear imaging, 3D-visualization and image-guided surgery, based on pre-operative data and tracked radiation detectors as described in the embodiments 15 or 16, further including: (a) monitoring the position and orientation and/or deformation of the body part that is imaged by use of a calibrated sensor; (b) computation of the relative positions and/or orientations and/or deformation of the body part that is imaged and of the radiation detector; and (c) compensation of movement and/or deformation of the body part that is imaged based on this relative position and orientation.

24. A method for intra-operative 3D-nuclear imaging, 3D-visualization and image-guided surgery, based on pre-operative data and tracked radiation detectors as described in the embodiments 15 or 16, further including: (a) using artificial markings positioned on or in the body part that is imaged; (b) tracking the position and orientation of the artificial markings; (c) determining the position and orientation of the body part that is imaged based on the position and orientation of the artificial markings; (d) calculating the relative positions and orientations of the body part that is imaged and of the radiation detector; and (e) compensation of the movement and/or deformation of the body part that is imaged based on this relative position and orientation.

25. A method for intra-operative 3D-nuclear imaging, 3D-visualization and image-guided surgery, based on pre-operative data and tracked radiation detectors as described in the embodiments 15 or 16, further including: (a) monitoring the respiration and the heart signal of the patient by means of a sensor; (b) determination of a phase for each reading, position and orientation of the radiation detector; (c) compensation of the movement and/or deformation because of respiration, heartbeat, or both based on these phases.

26. A method for intra-operative 3D-nuclear imaging, 3D-visualization and image-guided surgery, based on pre-operative data and tracked radiation detectors as described in any of the preceding or following embodiments, further including: (a) using at least one surgical instrument; (b) determining the relative positions and orientations of the surgical instruments and of the reconstructed 3D-image or registered pre-operative image; (c) using this relative position and orientation for (1) guiding instruments to regions of enhanced accumulation, (2) for guiding instruments away from regions of enhanced accumulation, (3) for guiding instruments to regions of low accumulation, (4) for guiding instruments away from regions of low accumulation, (5) for simulating, at the tip of each instrument, the radiation reading which would be given if each instrument were a gamma probe, (6) displaying surgical instruments on the display, and/or (7) for detecting and for warning a surgeon when the validity of the images is lost by the operation in the reconstructed and registered volume by means of the instruments.

27. A method for intra-operative 3D-nuclear imaging, 3D-visualization and image-guided surgery, based on pre-operative data and tracked radiation detectors as described in any of the preceding or following embodiments, further including: (a) displaying reconstructed images or registered pre-operative images either visually, acoustically, or haptically, or in a combined way in 3D, and/or in particular spatially registered with the imaging geometry of each camera.

28. A method for intra-operative 3D-nuclear imaging, 3D-visualization and image-guided surgery, based on pre-operative data and tracked radiation detectors as described in any of the preceding or following embodiments, further including: (a) a memory system for the full information or a part thereof for documentation purposes; and/or (b) generating an automatic report of the procedure.

29. A method for intra-operative 3D-nuclear imaging, 3D-visualization and image-guided surgery, based on pre-operative data and tracked radiation detectors as described in any of the preceding or following embodiments, further including: (a) online computation or tracking of errors in the position and orientation of any of the tracked objects and/or of the error in the reading of the radiation display; and (b) displaying the error for a signing a level of confidence to the readings and/or compensating the error for using the gathered information according to the level of confidence, and consequently to be able to correct the error.

30. A method for intra-operative 3D-nuclear imaging, 3D-visualization and image-guided surgery, based on pre-operative data and tracked radiation detectors substantially as described herein and with reference to/or as illustrated in the appended drawings.

In the following yet further additional embodiments are described (further embodiments 31 to 51):

31. A device for reliable intra-operative 3D-tomographic nuclear imaging, 3D-visualization of radioactive spatial distributions and image-guided surgery by use of radiation detectors, wherein the device includes: (a) a radiation detector; (b) a tracking system for tracking the position and orientation of the radiation detector in a synchronized way; (c) a first data processing unit which communicates with the radiation detector and the tracking system and which is able to evaluate the quality of the gathered data and to determine the necessary projections for reliable 3D-reconstructions; (d) a second data processing unit which communicates with the radiation detector and the tracking system and which is able to carry out a 3D-reconstruction based on the readings of the radiation detector and the corresponding positions and orientations; (e) a display that communicates with the data processing unit and is able to display the necessary projections for a reliable reconstruction to a surgeon and/or for guiding him; (f) a second display that communicates with the data processing unit and is able to display the valid reconstructed 3D-gamma emitting images to a surgeon and to thereby allow to guide him/her to improve the measurement.

32. A device for reliable intra-operative 3D-nuclear imaging, 3D-visualization of radioactive spatial distributions and image-guided surgery by use of radiation detectors, according to embodiment 31, wherein the first and second data processing units are the same or communicate with each other.

33. A device for reliable intra-operative 3D-nuclear imaging, 3D-visualization of radioactive spatial distributions and image-guided surgery by use of radiation detectors, according to embodiment 31, wherein the first and second display are the same or communicate with each other.

34. A device for reliable intra-operative 3D-nuclear imaging, 3D-visualization of radioactive spatial distributions and image-guided surgery by use of radiation detectors according to embodiment 31, wherein the radiation detector is one of the following: gamma probe, beta probe, gamma camera, beta camera, mini gamma camera, or a combination thereof 35. A device for reliable intra-operative 3D-nuclear imaging, 3D-visualization of radioactive spatial distributions and image-guided surgery by use of radiation detectors according to embodiment 31, wherein the tracking system is an external tracking system, which for example includes an optical tracking system, magnetic tracking system, mechanical or robot arm-based tracking system, a radio wave-based tracking system, a sound wave-based tracking system, etc. or an internal tracking system, which for example includes an acceleration detector-based tracking system, a potentiometer-based tracking system, etc., or any combination of an external tracking system and/or internal tracking system.

36. A device for reliable intra-operative 3D-nuclear imaging, 3D-visualization of radioactive spatial distributions and image-guided surgery by use of radiation detectors according to embodiment 31, wherein the display is one of the following: (a) a visual display, for example a monitor system, for example including: monitors and optically transparent monitors, stereo monitors, stereo-optical transparent head-mounted displays, etc.; (b) an acoustical display, for example including frequency-coded feedback systems, pulse-coded feedback systems, etc.; (c) a haptic display, for example including force feedback joysticks, force-torque feedback joysticks etc., or (d) a combination of visual, acoustical and/or haptic displays.

37. A method for reliable intra-operative 3D-nuclear imaging, 3D-visualization of radioactive spatial distributions and image-guided surgery by use of radiation detectors, including: (a) synchronized collection of readout data of the radiation detector and of the position and orientation of the radiation detector; (b) evaluation of the quality of the collected readout data, positions and/or orientations; (c) calculation of the necessary set of projections, which are needed to allow a reliable 3D-reconstruction; (d) displaying the set or a subset thereof or the information enabling to guide the surgeon to record the needed projections; (e) 3D-reconstruction of a valid 3D-gamma emitting image and/or the calculation of a corresponding quality value.

38. A method for reliable intra-operative 3D-nuclear imaging, 3D-visualization of radioactive spatial distributions and image-guided surgery by use of radiation detectors according to embodiment 31, including: (a) at least one surgical instrument; and (b) a second tracking system for tracking surgical instruments, wherein the second tracking system is the same as the first tracking system or communicates with the first tracking system, such that the relative position and orientation of the surgical instruments and of the reconstructed valid 3D-gamma emitting image can be calculated and can be used for (a) guiding the instruments to regions of high accumulation, (b) guiding the instruments away from regions of high accumulation, (c) guiding the instruments to regions of low accumulation, (d) guiding the instruments away from regions of low accumulation, (e) simulating, at the tip of each instrument, the radiation reading which would be given if each instrument was a radiation detector, (f) displaying surgical instruments on the display and/or (g) detecting and warning a surgeon, if the validity of the images is lost because of the invasion in the reconstructed volume by means of the instruments.

39. A method for reliable intra-operative 3D-nuclear imaging, 3D-visualization of radioactive spatial distributions and image-guided surgery by use of radiation detectors according to embodiment 35, wherein the relative position and orientation of surgical instruments is used for (a) guiding the instruments to regions of high accumulation, (b) guiding the instruments away from regions of high accumulation, (c) guiding the instruments to regions of low accumulation, (d) guiding the instruments away from regions of low accumulation, (e) calculating the radiation readings that surgical instruments at their given positions and orientations would measure if they were used as radiation detectors, (f) displaying the surgical instruments in co-registered form with the reconstructed valid 3D-gamma emitting images on the display, and/or (g) for detecting and for warning the surgeon if the validity of the images is lost by the invasion in the reconstructed volume by means of the instruments.

40. A device for reliable intra-operative 3D-nuclear imaging, 3D-visualization of radioactive spatial distributions and image-guided surgery by use of radiation detectors according to any of the preceding or following embodiments, further including: (a) a sensor for monitoring the respiration and the heart signal of a patient, wherein the sensor communicates with a data processing unit; (b) a sensor for determining the position and orientation and/or the deformation of the part of the body which is imaged with the system that communicates with a data processing unit, and/or (c) tracking markings placed on or in the body part that is imaged with the system and a third tracking system, wherein the third tracking system is the same as the first or the second tracking system or communicates with the first or second tracking system or communicates with the data processing units, such that each reading of the radiation detector, of the position and orientation and/or deformation can be calculated in the relation to the body part that is imaged or such that a phase label can be assigned to these with respect to the movement and/or the deformation cycles for allowing movement and/or deformation compensation in the reconstruction and/or the display.

41. A device for reliable intra-operative 3D-nuclear imaging, 3D-visualization of radioactive spatial distributions and image-guided surgery by use of radiation detectors according to any of the preceding or following embodiments, further including: (a) monitoring the respiration or a heart signal of the patient, (b) monitoring the position and orientation and/or the deformation of the body part that is imaged with the system, and/or (c) tracking the markings which are placed on or in the body part imaged with a system such that each reading of the radiation detector, position and orientation and/or deformation can be calculated relative to the body part that is imaged, or such that a phase label can be assigned thereto with respect to the movement and/or the deformation cycle for allowing movement and/or deformation compensation in the reconstruction and/or the display.

42. A device for reliable intra-operative 3D-nuclear imaging, 3D-visualization of radioactive spatial distributions and image-guided surgery by use of radiation detectors according to any of the preceding or following embodiments, further including: (a) a display of virtual reality and/or (b) a display of augmented reality, such that the reconstructed valid 3D-gamma emitting image can be displayed in 3D in acoustical, visual, or haptic way, or in a combined way, and/or in particular spatially registered with the image geometry of any camera, including laparoscope cameras and cameras based on surgical microscopes, optical and optically transparent head-mounted displays, optical and optically transparent stereoscopic surgical microscopes, optical and optically transparent displays.

43. A method for reliable intra-operative 3D-nuclear imaging, 3D-visualization of radioactive spatial distributions and image-guided surgery by use of radiation detectors according to any of the preceding or following embodiments, further including: displaying the reconstructed valid 3D-gamma emitting image on (a) a display of virtual reality and/or (b) a display of augmented reality, such that the image can be displayed in 3D in visual, acoustical, haptical or in a combined way, and/or in particular spatially registered with the image geometry of any camera, including laparoscope cameras and cameras based on surgical microscopes, optical and optically transparent head mounted displays, optical and optically transparent stereoscopic surgical microscopes, optical and optically transparent displays.

44. A device for reliable intra-operative 3D-nuclear imaging, 3D-visualization of radioactive spatial distributions and image-guided surgery by use of radiation detectors according to the embodiments 31, 37, 39, or 41, further including: (a) at least one 3D imaging device and a fourth tracking system that determines the position and orientation of the imaging device, and which is the same as the first, second or third tracking system or communicates with these and/or (b) at least one port for co-registered 3D-images, wherein the 3D imaging device, the fourth tracking system and the port for co-registered 3D-images communicates with the first and second data processing unit, such that the reconstructed valid 3D-gamma emitting image can be displayed in co-registered way with the 3D-images and/or can be used to execute attenuation and/or scattering correction on the 3D-gamma emitting images, which are for example ultrasonic images, x-ray based images, magnetic resonance tomography images, optical images, contrast-enhanced ultrasonic images, contrast-enhanced x-ray based images, functional magnetic resonance tomography images, dye-based optical images, fluorescence images, reflection images, auto-fluorescence images, etc.

45. A method for reliable intra-operative 3D-nuclear imaging, 3D-visualization of radioactive spatial distributions and image-guided surgery by use of radiation detectors according to any of the preceding or following embodiments, further including: (a) co-registered acquisition of anatomical or functional images that stem from at least one 3D device and/or (b) use of previously acquired co-registered 3D images that stem from at least one 3D image generating device, such that the reconstructed valid 3D-gamma emitting images can be displayed in co-registered way with the 3D images and/or such that the 3D-gamma emitting images can be corrected with respect to attenuation and/or scattering by use of 3D images.

46. A device for reliable intra-operative 3D-nuclear imaging, 3D-visualization of radioactive spatial distributions and image-guided surgery, preferably by use of radiation detectors, according to any of the preceding or following embodiments, further including: (a) a memory system for the involved information which communicates with a first and second data processing unit and/or (b) a third data processing unit which communicates with a first and second data processing unit, such that the full information or a part thereof are stored as documentation material and/or an automatic report of the procedure is generated.

47. A method for reliable intra-operative 3D-nuclear imaging, 3D-visualization of radioactive spatial distributions and image-guided surgery by use of radiation detectors according to any of the embodiments 36, 38, 40, 42, or 44, further including: (a) storing the involved information and/or (b) automatically generating documentation material.

48. A device for reliable intra-operative 3D-nuclear imaging, 3D-visualization of radioactive spatial distributions and image-guided surgery by use of radiation detectors as described in any of the preceding or following embodiments, further including: a sensor and/or a further data processing unit, which can be the same as the first data processing unit or can communicate with the first data processing unit, for online computation or tracing errors in the position and orientation of each of the tracked objects and/or of the error in the readout data of the radiation readings.

49. A method for reliable intra-operative 3D-nuclear imaging, 3D-visualization of radioactive spatial distributions and image-guided surgery by use of radiation detectors as described in any of the preceding or following embodiments, further including: (a) online calculation or tracing of errors in the position and orientation of each of the tracked objects and/or of the error in the readout of each radiation reading; and (b) displaying the error to assign a level of confidence and/or compensating the error to use the gathered information according to the level of confidence and to thus be able to compensate the errors.

50. A device for reliable intra-operative 3D-nuclear imaging, 3D-visualization of radioactive spatial distributions and image-guided surgery by use of radiation detectors substantially as described herein and with reference to and/or as illustrated in the appended drawings.

51. A method for reliable intra-operative 3D-nuclear imaging, 3D-visualization of radioactive spatial distributions and image-guided surgery by use of radiation detectors substantially as described herein and with reference to and/or as illustrated in the appended drawings.

While the forgoing is directed to embodiments of the invention, other and further embodiments of the invention can be devised without departing from the scope of the invention set forth in the following claims.

The invention claimed is:

1. A method for generating an image of a nuclear radiation source, the method comprising:
   detecting nuclear radiation of the nuclear radiation source by a movable detector during a detection period;
   tracking position and orientation of the movable detector by a tracking system during the detection period;
   collecting detector data by an evaluation system during the detection period, wherein the detector data comprises information about the detected nuclear radiation and comprises information about positions and orientations of the movable detector, wherein the information about detected nuclear radiation is synchronized with the information about positions and orientations of the movable detector;
   enhancing a linear imaging rule by the evaluation system during the detection period, comprising:
      determining an imaging matrix based on the detector data collected by the evaluation system;
      determining at least one quality value of the imaging matrix with respect to at least one corresponding quality criterion; and
      modifying the imaging matrix based on the at least one quality value to create a modified imaging matrix;
   generating an image of the nuclear radiation source based on the modified imaging matrix using the evaluation system; and
   outputting the image of a nuclear radiation source on an output system.

2. The method according to claim 1, wherein modifying the imaging matrix based on the-at least one quality value during the detection period leads to an enhancement of the at least one quality value with respect to the at last one quality criterion.

3. The method according to claim 1, wherein:
the at least one quality value is selected from a group consisting of the sparsity of a row of the imaging matrix, the sparsity of a column of the imaging matrix, the relevance of a row of the imaging matrix, and the relevance of a column of the imaging matrix, wherein the sparsity of a row of the imaging matrix is the number of entries in the row different from zero, the sparsity of a column of the imaging matrix is the number of entries in the column different from zero, the relevance of a row of the imaging matrix is the sum of all entries of the row, and the relevance of a column of the imaging matrix is the sum of all entries of the column; and
the at least one quality criterion is correspondingly selected from the group consisting of: a threshold value for the sparsity of the row, a threshold value for the sparsity of the column, a threshold value for the relevance of the row, and a threshold value for the relevance of the column.

4. The method according to claim 1, wherein modifying the imaging matrix comprises at least one of the following: elimination of a row of the imaging matrix whose sparsity is below a threshold value, elimination of a column of the imaging matrix whose sparsity is below a threshold value, elimination of a row of the imaging matrix whose relevance is below a threshold value, and elimination of a column of the imaging matrix whose relevance is below a threshold value.

5. The method according to claim 1, wherein modifying the imaging matrix comprises at least one of the following: a combination of a row of the imaging matrix whose sparsity is below a threshold value with another row, a combination of a column of the imaging matrix whose sparsity is below a threshold value with another column, a combination of a row of the imaging matrix whose relevance is below a threshold value with another row, and a combination of a column of the imaging matrix whose relevance is below a threshold value with another column.

6. The method according to claim 5, wherein a higher weight is attributed to a combined row or a combined column in the generation of the image of the nuclear radiation source.

7. The method according to claim 1, wherein collecting the detector data comprises collecting the detector data in a vector, and wherein enhancing the linear imaging rule comprises eliminating or combining entries in the vector containing the detector data.

8. The method according to claim 1, wherein the linear imaging rule comprises an application of the imaging matrix to a first vector whose entries are image elements, wherein the entries of the first vector comprise information about the spatial distribution of the nuclear radiation source obtained from a comparison image.

9. The method according to claim 8, wherein enhancing the linear imaging rule includes modifying the first vector by eliminating or combining entries thereof.

10. The method according to claim 1, wherein generating the image of the nuclear radiation source comprises minimizing the distance |H*f−g_measured| over all estimated radiation distributions, the image information of which is coded into a respective vector f of image elements, wherein |•| denotes a distance norm, H is the modified imaging matrix, and g_measured is a vector containing the collected detector data.

11. The method according to claim 10, wherein the minimization starts with a first vector of image elements, wherein the entries of the first vector comprise information about the spatial distribution of the nuclear radiation source obtained from a comparison image.

12. The method according to claim 1, wherein generating the image of the nuclear radiation source comprises a minimization by an algorithm selected from the group of: best-neighbour ansatz, simplex-optimizer, Levenberg-Marquardt algorithm, steepest gradient descent, and conjugate gradient descent.

13. The method according to claim 1, wherein the detector data are continuously collected during the detection period, wherein the at least one quality value is repeatedly determined during the detection period with respect to the corresponding at least one quality criterion, and wherein the imaging matrix is repeatedly modified on the basis of the repeatedly determined at least one quality value during the detection period.

14. The method according to claim 1, wherein enhancing the linear imaging rule by the evaluation system during the detection period comprises outputting an instruction to a user by the output system, wherein the instruction depends on the at least one determined quality value and instructs the user to move the movable detector in a particular way to improve the at least one determined quality value, wherein the instruction relates to at least a part of the remaining detection period.

15. The method according to claim 1, comprising: outputting the at least one determined quality value to a user by the output system.

16. The method according to claim 1, wherein the image of the radiation source is a three-dimensional image.

17. An image generating apparatus for generating an image of a nuclear radiation source, comprising:
a movable detector for detecting nuclear radiation of the nuclear radiation source during a detection period;
a tracking system for gathering data about positions and orientations of the movable detector during the detection period; and
an evaluation system, comprising:
a detector system interface for exchanging data with the movable detector during the detection period;
a tracking system interface for exchanging data with the tracking system during the detection period;
a data memory portion for storing detector data transmitted from the detector system interface and from the tracking system interface during the detection period, wherein the detector data comprises information about the detected nuclear radiation and comprises information about the positions and orientations of the detector, wherein the information about the detected nuclear radiation is synchronized with the information about the positions and orientations of the detector; and
a program memory portion with programs for enhancing a linear imaging rule during the detection period, the enhancing comprising:
determining an imaging matrix based on the detector data;
determining at least one quality value of the imaging matrix with respect to at least one corresponding quality criterion; and
modifying the imaging matrix based on the determined at least one quality value to create a modified imaging matrix;
wherein the evaluation system generates an image of the nuclear radiation source on the basis of the modified imaging matrix; and wherein the image generating apparatus further comprises an output system for outputting the image of the nuclear radiation source.

18. The image generating apparatus according to claim 17, wherein:
the at least one quality value is selected from a group consisting of: the sparsity of a row of the imaging matrix, the sparsity of a column of the imaging matrix, the relevance of a row of the imaging matrix, and the relevance of a column of the imaging matrix, wherein the sparsity of a row of the imaging matrix is the number of entries in the row different from zero, the sparsity of a column of the imaging matrix is the number of entries in the column different from zero, the relevance of a row of the imaging matrix is the sum of all entries of the row, and the relevance of a column of the imaging matrix is the sum of all entries of the column; and
the at least one quality criterion is correspondingly selected from the group consisting of a threshold value for the sparsity of the row, a threshold value for the sparsity of the column, a threshold value for the relevance of the row, and a threshold value for the relevance of the column.

19. The image generating apparatus according to claim 17, wherein modifying the imaging matrix comprises at least one of the following: elimination of a row of the imaging matrix whose sparsity is below a threshold value, elimination of a column of the imaging matrix whose sparsity is below a threshold value, elimination of a row of the imaging matrix whose relevance is below a threshold value, and elimination of a column of the imaging matrix whose relevance is below a threshold value.

20. The image generating apparatus according to claim 17, wherein modifying the imaging matrix comprises at least one of the following: a combination of a row of the imaging matrix whose sparsity is below a threshold value with another row, a combination of a column of the imaging matrix whose sparsity is below a threshold value with another column, a combination of a row of the imaging matrix whose relevance is below a threshold value with another row, and a combination of a column of the imaging matrix whose relevance is below a threshold value with another column.

* * * * *